(12) United States Patent
Odom et al.

(10) Patent No.: US 10,153,510 B2
(45) Date of Patent: Dec. 11, 2018

(54) NON-AQUEOUS REDOX FLOW BATTERIES INCLUDING 3,7-PERFLUOROALKYLATED PHENOTHIAZINE DERIVATIVES

(71) Applicant: University of Kentucky Research Foundation, Lexington, KY (US)

(72) Inventors: Susan A. Odom, Lexington, KY (US); Aman P. Kaur, Lexington, KY (US); Corrine F. Elliott, Lexington, KY (US); Matthew D. Casselman, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 373 days.

(21) Appl. No.: 14/747,816

(22) Filed: Jun. 23, 2015

(65) Prior Publication Data
US 2015/0372333 A1 Dec. 24, 2015

Related U.S. Application Data

(60) Provisional application No. 62/015,954, filed on Jun. 23, 2014.

(51) Int. Cl.
*H01M 8/18* (2006.01)
*C07D 279/22* (2006.01)
(Continued)

(52) U.S. Cl.
CPC .......... *H01M 8/188* (2013.01); *C07D 279/22* (2013.01); *C07D 279/30* (2013.01); *H01M 8/20* (2013.01);
(Continued)

(58) Field of Classification Search
CPC ............... H01M 8/188; H01M 8/20; H01M 2300/0028; H01M 2300/0025; C07D 279/22; C07D 279/30; Y10T 29/4911
See application file for complete search history.

(56) References Cited

U.S. PATENT DOCUMENTS 3,419,553 A 12/1968 Bernstein et al.
3,719,671 A 3/1973 Wu et al.
(Continued)

OTHER PUBLICATIONS

"Overcharge performance of 3,7-disubstituted N-ethylphenothiazine derivatives in lithium-ion batteries." Chem. Commun. 2014 50, 5339-5341, by Odom et al., available Nov. 2013 (Year: 2013).*
(Continued)

*Primary Examiner* — Michael L Dignan
(74) *Attorney, Agent, or Firm* — Mandy Wilson Decker; Stites & Harbison PLLC

(57) ABSTRACT

A non-aqueous redox flow battery includes a negative electrode immersed in a first non-aqueous liquid electrolyte solution, a positive electrode immersed in a second non-aqueous liquid electrolyte solution, and a semi-permeable separator interposed between the negative and positive electrodes, wherein the second the non-aqueous liquid electrolyte solution comprises a compound of the formula:

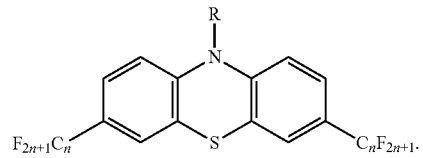

20 Claims, 10 Drawing Sheets

(51) Int. Cl.
*C07D 279/30* (2006.01)
*H01M 8/20* (2006.01)
(52) U.S. Cl.
CPC ............... *H01M 2300/0025* (2013.01); *H01M 2300/0028* (2013.01); *Y10T 29/4911* (2015.01)

(56) References Cited

U.S. PATENT DOCUMENTS

| | | | |
|---|---|---|---|
| 4,397,922 | A | 8/1983 | Pokhodenko et al. |
| 4,869,977 | A | 9/1989 | Connolly et al. |
| 5,976,731 | A | 11/1999 | Negoro et al. |
| 7,407,948 | B2 | 8/2008 | Griffiths et al. |
| 7,407,953 | B2 | 8/2008 | Brown et al. |
| 7,615,312 | B2 * | 11/2009 | Dahn ............... H01M 10/0525 29/623.1 |
| 7,885,590 | B2 | 2/2011 | Seo et al. |
| 8,257,870 | B2 | 9/2012 | Horikawa |
| 8,785,434 | B2 | 7/2014 | Hurt et al. |
| 2003/0158204 | A1 | 8/2003 | Galey |
| 2010/0204215 | A1 | 8/2010 | Galey et al. |
| 2011/0178071 | A1 | 7/2011 | Plattner et al. |
| 2012/0302675 | A1 | 11/2012 | Sakamoto et al. |
| 2012/0328530 | A1 | 12/2012 | Wainwright |
| 2013/0224538 | A1 * | 8/2013 | Jansen ................ H01M 8/188 429/72 |
| 2013/0230771 | A1 | 9/2013 | Deronzier et al. |
| 2014/0058099 | A1 | 2/2014 | Wakamiya et al. |
| 2014/0070146 | A1 | 3/2014 | Parham et al. |
| 2014/0114063 | A1 | 4/2014 | Itio |
| 2014/0155591 | A1 | 6/2014 | Takada |
| 2014/0178735 | A1 * | 6/2014 | Wang ..................... H01M 8/20 429/105 |
| 2014/0308317 | A1 | 10/2014 | Fan et al. |
| 2015/0011712 | A1 | 1/2015 | Chaix et al. |

OTHER PUBLICATIONS

Yang, et al., Electrochemical Energy Storage for Green Grid, Chemical Reviews, 2011, 111, 3577-3613.
Liu, et al., Materials Science and Materials Chemistry for Large Scale Electrochemical Energy Storage: From Transportation to Electrical Grid, Advanced Functional Materials, 2013, 23, 929-946.
Darling, et al., Pathways to low-cost electrochemical energy storage: a comparison of aqueous and nonaqueous flow batteries, Energy Environ. Sci., 2014, 7, 3459-3477.
Kinter-Myer, National Assessment of Energy Storage for Grid Balancing and Arbitrage:Phase 1, WECCPNNL Report, 2012, 1-204.
Parasuraman, et al., Review of material research and development for vanadium redox flow battery applications, Electrochimica Acta, 2013, 101, 27-40.
Leung, et al., Progress in redox flow batteries, remaining challenges and their applications in energy storage, RSC Advances, 2012, 2, 10125-10156.
Skyllas-Kazacos, et al., Progress in Flow Battery Research and Development, Electrochem. Soc., 2011, 158, R55-R79.
Kamath, et al., Vanadium Redox Flow Batteries: An InDepth Analysis, EPRI, Palo Alto, CA, 2007.
Xu, Nonaqueous Liquid Electrolytes for Lithium-Based Rechargeable Batteries, Chem. Rev., 2004, 104, 4303-4417.
Matsuda, et al., A rechargeable redox battery utilizing ruthenium complexes with non-aqueous organic electrolyte, J Appl Electrochem, 1988, 18, 909-914.
Yamamura, et al., Electrochemical investigation of uranium b-diketonates for all-uranium redox flow battery, Electrochimica Acta, 2002, 48, 43-50.

Bae, et al., Chromium redox couples for application to redox flow batteries, Electrochimica Acta, 2002, 48, 279-287.
Chakrabarti, et al., Evaluation of electrolytes for redox flow battery applications, Electrochimica Acta, 2007, 52, 2189-2195.
Liu, et al., Non-aqueous vanadium acetylacetonate electrolyte for redox flow batteries, Electrochemistry Communications, 2009, 11, 2312-2315.
Liu, et al., Non-aqueous chromium acetylacetonate electrolyte for redox flow batteries, Electrochemistry Communications, 2010, 12, 1634-1637.
Chakrabarti, et al., Ruthenium based redox flow battery for solar energy storage, Energy Conversion and Management, 2011, 52, 2501-2508.
Sleightholme, et al., Non-aqueous manganese acetylacetonate electrolyte for redox flow batteries, Journal of Power Sources, 2011, 196, 5742-5745.
Herr, et al., Increasing the energy density of the non-aqueous vanadium redox flow battery with the acetonitrile-1,3-dioxolaneedimethyl sulfoxide solvent mixture, Journal of Power Sources, 2014, 265, 317-324.
Li, et al., Electrochemical Properties of an All-Organic Redox Flow Battery Using 2,2,6,6-Tetramethyl-1-Piperidinyloxy and N-Methylphthalimide, Electrochemical and Solid-State Letters, 2011, 14, A171-A173.
Wang, et al., Anthraquinone with tailored structure for a nonaqueous metal-organic redox flow battery Chemical Communications, 2012, 48, 6669-6671.
Brushett, et al., An All-Organic Non-aqueous Lithium-Ion Redox Flow Battery Advanced Energy Materials, 2012, 2, 1390-1396.
Su, et al., Electrolyte Development for Non-Aqueous Redox Flow Batteries Using a High-Throughput Screening Platform, J. Electrochem. Soc., 2014, 161, A1905-A1914.
Huang, et al., Liquid Catholyte Molecules for Nonaqueous Redox Flow Batteries, Advanced Energy Materials, 2015, 10.1002/aenm. 201401782.
Hamelet, et al., Silicon-Based Non Aqueous Anolyte for Li Redox-Flow Batteries, Journal of the Electrochemical Society, 2013, 160, A516-A520.
Oh, et al., A metal-free and all-organic redox flow battery with polythiophene as the electroactive species, J. Mat. Chem. A, 2014, 2, 19994-19998.
Surendran, et al., Reduction potential predictions of some aromatic nitrogen-containing molecules, RSC Advances, 2014, 4, 57442.
Kaur, et al., 3,7-Bis(trifluoromethyl)-N-ethylphenothiazine: a redox shuttle with extensive overcharge protection in lithium-ion batteries, J. Mat. Chem. A, 2014, 2, 18190-18193.
Ergun, et al., Overcharge performance of 3,7-disubstituted N-ethylphenothiazine derivatives in lithium-ion batteries, Chem. Commun., 2014, 50, 5339-5341.
Zhang, et al., Molecular engineering towards safer lithium-ion batteries: a highly stable and compatible redox shuttle for overcharge protection, Energy Environ. Sci., 2012, 5, 8204-8207.
Narayana, et al., N-Substituted Phenothiazine Derivatives: How the Stability of the Neutral and Radical Cation Forms Affects Overcharge Performance in Lithium-Ion Batteries, ChemPhysChem, 2015, 16, 1179-1189.
Casselman, et al., The fate of phenothiazine-based redox shuttles in lithium-ion batteries, Phys.Chem.Chem.Phys., 2015, 17, 6905.
Shin, et al., A review of current developments in non-aqueous redox flow batteries: characterization of their membranes for design perspective, RSC Advances, 2013, 3, 9095-9116.
Kaur, et al., "A Highly Soluble Organic Catholyte for Non-Aqueous Redox Flow Batteries." * Energy Technology, 2015, 3, 476-480.
Kaur, et al., "Overcharge Performance of 3,7-Bis(trifluoromethyl)-N-ethylphenothiazine at High Concentrations in Lithium-Ion Batteries." * Journal of the Electrochemical Society, 2016, 163, A1-A7.

* cited by examiner

NON-AQUEOUS REDOX FLOW BATTERIES INCLUDING 3,7-PERFLUOROALKYLATED PHENOTHIAZINE DERIVATIVES

RELATED APPLICATIONS

This application claims the benefit of U.S. Provisional Patent Application No. 62/015,954, filed Jun. 23, 2014, the entire disclosure of which is hereby incorporated by reference.

GOVERNMENT INTEREST

This invention made with government support under grant number 1200653 awarded by the National Science Foundation. The government has certain rights in the invention.

TECHNICAL FIELD

The presently-disclosed subject matter includes non-aqueous redox batteries and compounds for use in non-aqueous redox batteries. More particularly, the presently disclosed subject matter relates to non-aqueous redox flow batteries including unique, 3,7-perfluoroalkylated phenothiazine derivatives.

INTRODUCTION

As greenhouse gases continue to warm the Earth, increasing the number of renewable energy sources connected to the electrical grid has become a topic of worldwide interest. (1-3) The current electrical grid is predicted to become unstable if solar and wind power rise to supply more than 20% of its energy—a benchmark which we are predicted to reach by 2030—because the grid lacks the ability to accommodate fluctuating energy sources.(4) To remedy this limitation, large-scale electrical energy storage (EES) systems have been investigated for the purpose of storing energy during peak production and releasing it to relieve strain on the grid during periods of peak end-user demand, resulting in a load-levelling effect.(5)

For grid storage using EES, aqueous redox flow batteries (RFBs) have shown great promise due to their low costs and long lifetimes(7, 8) and have been demonstrated on scales up to 10 MW.(8, 9) Of the many flow systems that have been investigated, the aqueous all-vanadium system is the most advanced.(10) However, the voltage window of aqueous systems is limited to ca. 1.5 V by the electrolysis of water, and they employ high concentrations of extremely corrosive supporting electrolytes such as sulfuric acid, hydrobromic acid, hydrochloric acid, or nitric acid.(7, 8) These two detriments have led to increased interest in non-aqueous redox flow systems, which can potentially be charged to 4 V, depending on the solvent used.(11) Half- and full-cell designs have been demonstrated on small scales, employing a variety of solvents and a handful of electro-active materials as the electron donors and acceptors,(12-20) including phthalimide, anthracene, quinone, or quinoxilane derivatives as the anolyte(21-23) and TEMPO or dimethoxybenzene derivatives as the catholyte.(21, 23-25) Recently, suspensions of solid electrode materials used in Li-ion batteries have also been reported for use as the charge-carrying electro-active species.(26)

The main factors preventing commercialization of non-aqueous RFBs are the poor voltages and energy efficiencies and the rapid decay in capacity with cycling. These faults are attributed to one or more of the following problems with the electro-active species: limited stability of oxidized and/or reduced forms, irreversible reaction with electrode surfaces, and membrane crossover. Despite the development of functionalized derivatives (23, 25) and tailored electrolytes(3, 15, 20, 24) for increased solubility, instances of battery cycling reported in the majority of non-aqueous RFB publications have been limited to systems with low concentrations of the electro-active species (≤0.05 M), perhaps due to more rapid capacity fade when electro-active materials are tested at higher concentrations. The ability to tailor the structure of organic compounds to lead to more soluble, more stable species offers an opportunity to improve upon these limiting factors.

There exists a need for high stability, relatively highly soluble electroactive materials that can be used in non-aqueous redox flow batteries and non-aqueous redox flow batteries with commercial use. Compounds that can dissolve at relatively high concentrations can lead to higher capacity redox flow batteries that make high capacity batteries capable of commercialization.

SUMMARY

The presently disclosed subject matter includes a non-aqueous redox flow battery and method of making the same, comprising a negative electrode immersed in a first non-aqueous liquid electrolyte solution, positive electrode immersed in a second non-aqueous liquid electrolyte solution, a semi-permeable separator interposed between the negative and positive electrodes, and the second non-aqueous liquid electrolyte solution comprises a compound of the formula:

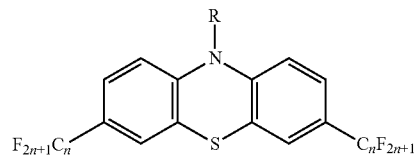

wherein R is selected from alkyl, aryl, alkylaryl, alkoxyaryl, alkylcarboxyl, aryl carbonyl, haloalkyl, perfluoroalkyl, glycols, haloaryl, a negative electrolyte, and a polymer; and wherein each n is independently an integer from 1 to 6.

The presently-disclosed subject matter also includes materials comprised of novel phenothiazine compounds. The novel phenothiazine compounds of the present invention are N-substituted and comprise one or more electron withdrawing groups substituted para to the N-group. Exemplary compounds can be stable neutral and oxidized (radical cation) states, exhibit relatively high oxidation potentials, and high solubility, and can increase capacity of non-aqueous all-organic redox flow batteries.

In some embodiments, the novel phenothiazine compounds can be used in non-aqueous redox flow batteries. In some embodiments, during charging, the present compounds become oxidized to form their radical cations while another component of the battery accepts electrons and becomes negatively charged. During discharging, the electron is transferred back to one of the phenothiazine derivatives. In some embodiments, because the second oxidation can be reversible, it can be possible to form the dication (i.e., two electron transfer reactions) during charging.

DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
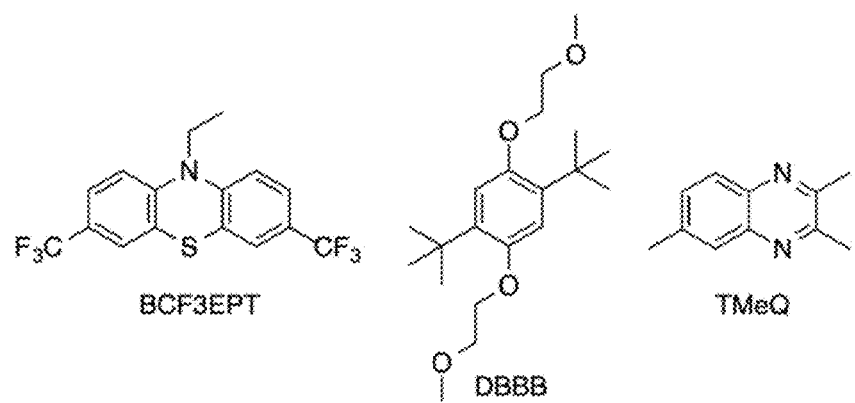
FIG. 1: Chemical structures of the catholytes 3,7-bis(trifluoromethyl)-N-ethylphenothiazine (BCF3EPT) and 2,5-di-tert-butyl-1,4-bis(2-methoxyethoxy)benzene (DBBB), and the anolyte 2,3,6-trimethyl quinoxaline (TMeQ).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes N-substituted phenothiazine compounds, substituted, for example, para to the Nitrogen. In some embodiments, substitutions occur at the 3 and 7 positions of the ring. In some embodiments, the phenothiazine compounds used for positive electrolyte solutions are functionalized with $CF_3$ groups. The compounds according to the presently disclosed subject matter can be used for non-aqueous redox flow batteries with high capacities and have commercial viability.

The presently-disclosed subject matter also includes novel phenothiazine compounds. The novel phenothiazine compounds are suitable for use, for example, in non-aqueous redox flow batteries. During charging, the present compounds become oxidized to form their radical cations while another component of the battery accepts electrons and becomes negatively charged. During discharging, the electron is transferred back to one of the phenothiazine derivatives. In some embodiments, because the second oxidation can be reversible, it can be possible to form the dication (i.e., two electron transfer reactions) during charging.

As described herein, the present inventors have characterized the present compounds by cyclic voltammetry and overcharge cycling. Concentrations of the compounds can range from 0.0001 M to about 5.0 M. For overcharge protection studies, derivatives were suspended or dissolved in a carbonate solvent, sometimes a combination of ethylene carbonate and ethylmethyl carbonate, containing 0.5-1.2 M lithium salt such as $LiPF_6$ or $LiBF_4$. Demonstrations of overcharge protection over an extended time period indicate that the oxidized states of the compounds are stable and suggest that this class of compounds will serve as effective positive electrode materials in redox flow batteries, wherein it is beneficial to include electrode materials that are stable when oxidized.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds.

Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms such as "R", such terms are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term. The term "alkyl" is inclusive of "cycloalkyl."

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

In this regard, the term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. The term is include of linear and ring-forming (i.e., cycloakenyl) groups. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, haide, hydroxy, ketone, azide, nitro, silyl, sulfo-oxo, or thiol, as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by a formula —C(O)H. Throughout this specification "C(O)" is a short hand notation for a carbonyl group, i.e., C=O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein. In specific embodiments amine refers to any of $NH_2$, NH(alkyl), NH(aryl), N(alkyl)$_2$, and N(aryl)$_2$.

The term "carboxylic acid" as used herein is represented by a formula —C(O)OH.

The term "ester" as used herein is represented by a formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by a formula -(A$^1$O(O)C-A$^2$-C(O)O)$_a$— or -(A$^1$O(O)C-A$^2$-OC(O))$_a$—, where A$^1$ and A$^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "halide," "halogen," or the like refer to the halogens fluorine, chlorine, bromine, and iodine.

The term "thiol" as used herein is represented by a formula —SH.

The term "polymer," when used herein to refer to R of the compounds disclosed herein, includes vinyl polymers, including but not limited to ethylene, propylene, and styryl polymers, cyclic alkenes, including for example norbornene, norbornadiene, cyclopentene, and cyclooctatetraene, acrylates, amines, epoxies, isocyanates, and the like. Also, as used herein, polymer refers to linear polymers as well as other arrangements, including for example, dendrimer, star, and hyper branched polymers. In some embodiments, the polymer can include phenothiazine as the sole monomer in a repeating polymer. In some embodiments, the polymer can include phenothiazine as part of a polymer that contains more than one repeat unit, e.g., alternating copolymer or block copolymer.

The presently-disclosed subject matter also includes derivatives of any of the compounds described herein. As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

The compounds described herein can contain one or more double bonds and, thus, potentially can give rise to cis/trans (E/Z) isomers, as well as other conformational isomers. Unless stated to the contrary, the invention includes all such possible isomers, as well as mixtures of such isomers. Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

The presently disclosed subject matter includes a non-aqueous redox flow battery comprising a negative electrode immersed in a first non-aqueous liquid electrolyte solution, positive electrode immersed in a second non-aqueous liquid electrolyte solution, a semi-permeable separator interposed between the negative and positive electrodes, and the second non-aqueous liquid electrolyte solution comprises a compound of the formula:

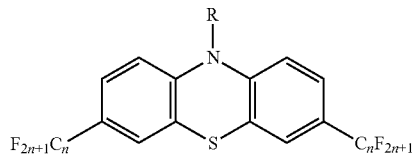

wherein R is selected from alkyl, aryl, alkylaryl, aloxyarul, alkylcarboxyl, aryl carbonyl, haloalkyl, perfluoroalkyl, glycols, haloaryl, a negative electrolyte, and a polymer; and wherein each n is independently an integer from 1 to 6.

The presently disclosed invention includes a positive cell comprising a cathode and a compound according to the formula:

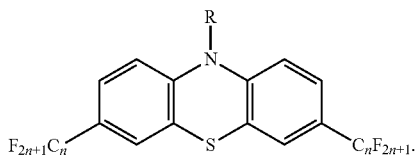

wherein R is selected from alkyl, aryl, alkylaryl, aloxyarul, alkylcarboxyl, aryl carbonyl, haloalkyl, perfluoroalkyl, glycols, haloaryl, a negative electrolyte, and a polymer; and wherein each n is independently an integer from 1 to 6.

The compound in the non-aqueous solvent of the presently disclosed battery can, in some embodiments, be:

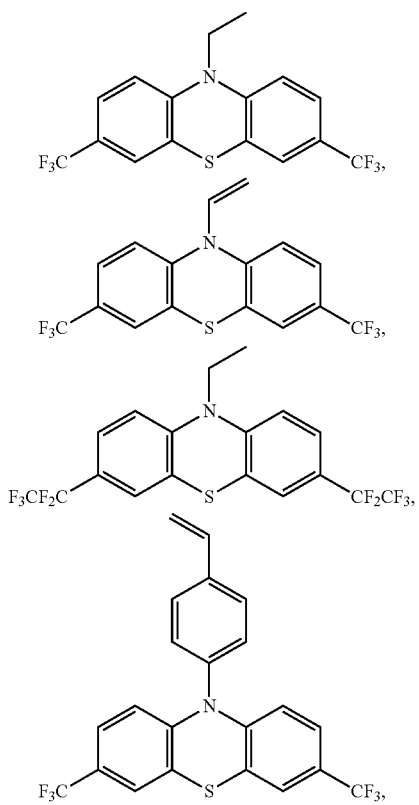

-continued
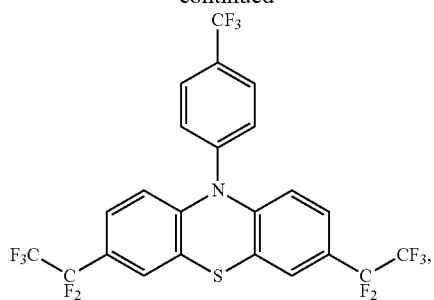
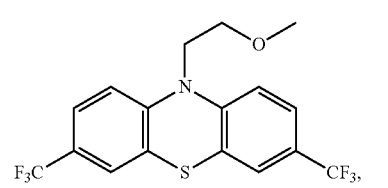
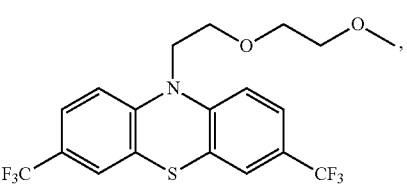
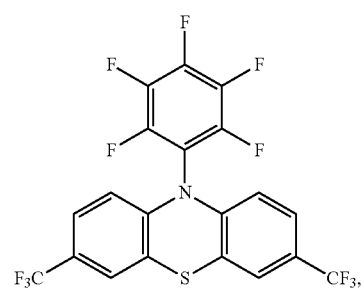
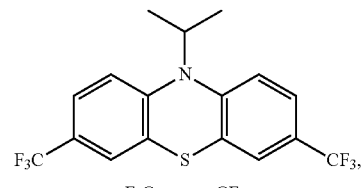
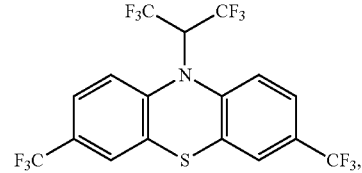
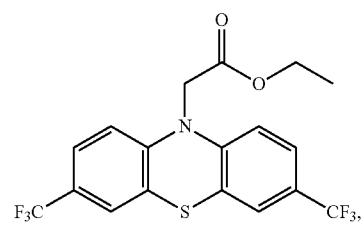
-continued
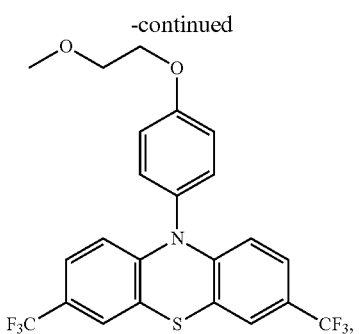
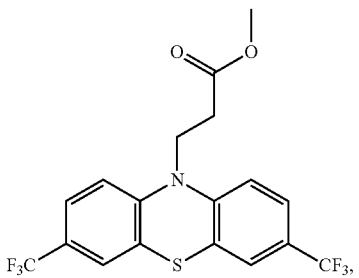
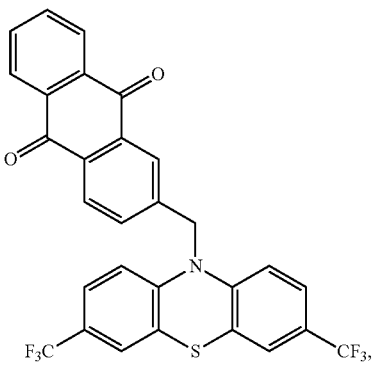
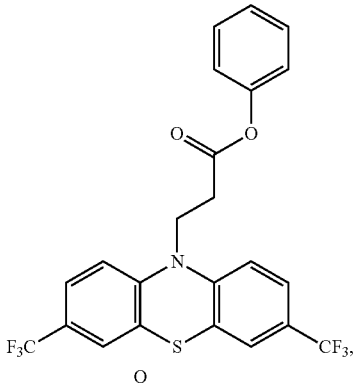
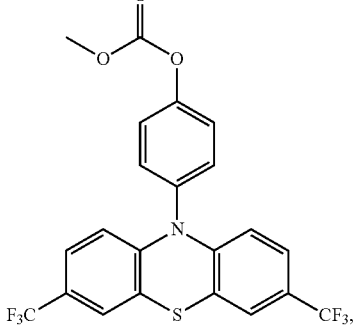

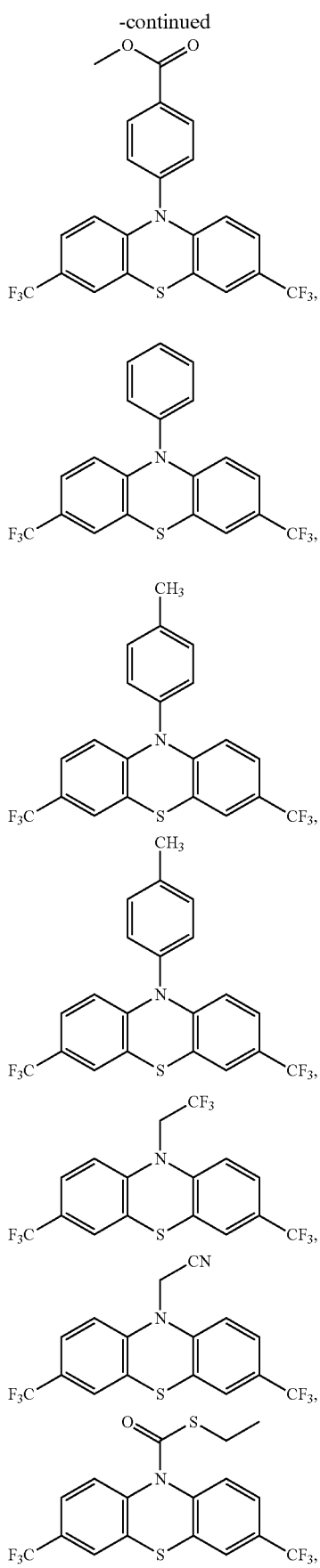
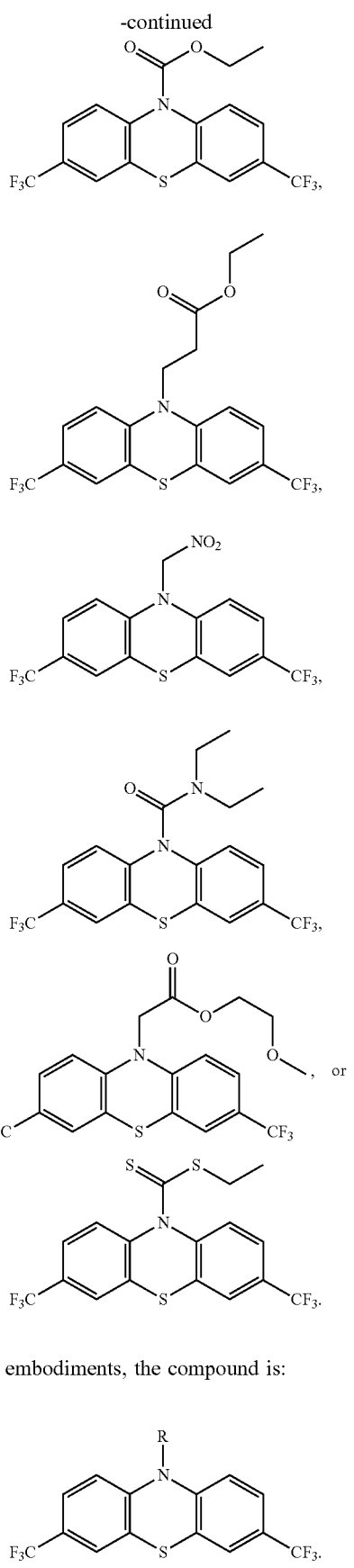
In other embodiments, the compound is:
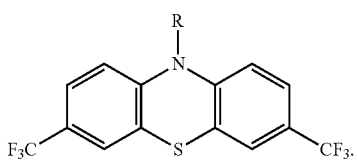

In some embodiments, the compound can include a polymer. An example of a polymer structure can be:

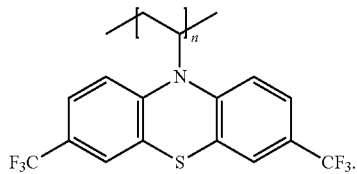

When the compound includes a polymer, the polymerization occurs at the R group. The R group can be, for example, a vinyl group, for example, ethylene, propylene, styryl, cyclic alkenes, for example, norbornene, norbornadiene, cyclopentene, cyclooctatetraene, acrylates, amines, epoxies, and isocyanates. In some embodiments, the polymer is a branched polymer, a hyperbranched polymer, a dendrimer, a star, a dendron or a mixture thereof. In some embodiments the compound of the present invention is a block co-polymer. In some instances, the block polymers are diblock polymers or triblock polymers. In some instances the block polymers can be AB type polymers or ABC type polymers. can be, for example A-B, A-A-B-B.

The presently disclosed subject matter is also directed to making a non-aqueous redox flow battery. The method of making a non-aqueous redox flow battery includes immersing a negative electrode in a first non-aqueous liquid electrolyte solution, immersing a positive electrode in a second non-aqueous liquid electrolyte solution, and interposing a semi-permeable separator between the negative and positive electrodes. The second non-aqueous liquid electrolyte solution comprises a compound of the formula:

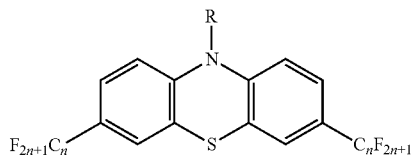

wherein R is selected from alkyl, aryl, alkylaryl, alkoxyaryl, alkylcarboxyl, aryl carbonyl, haloalkyl, perfluoroalkyl, glycols, haloaryl, a negative electrolyte, and a polymer; and wherein each n is independently an integer from 1 to 6.

Representative compounds of the presently disclosed invention include:

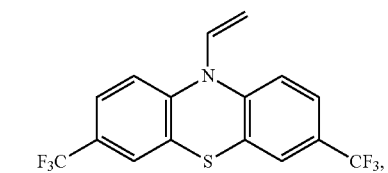

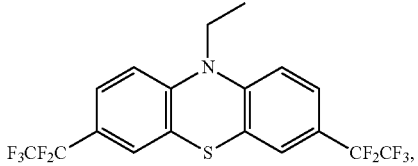

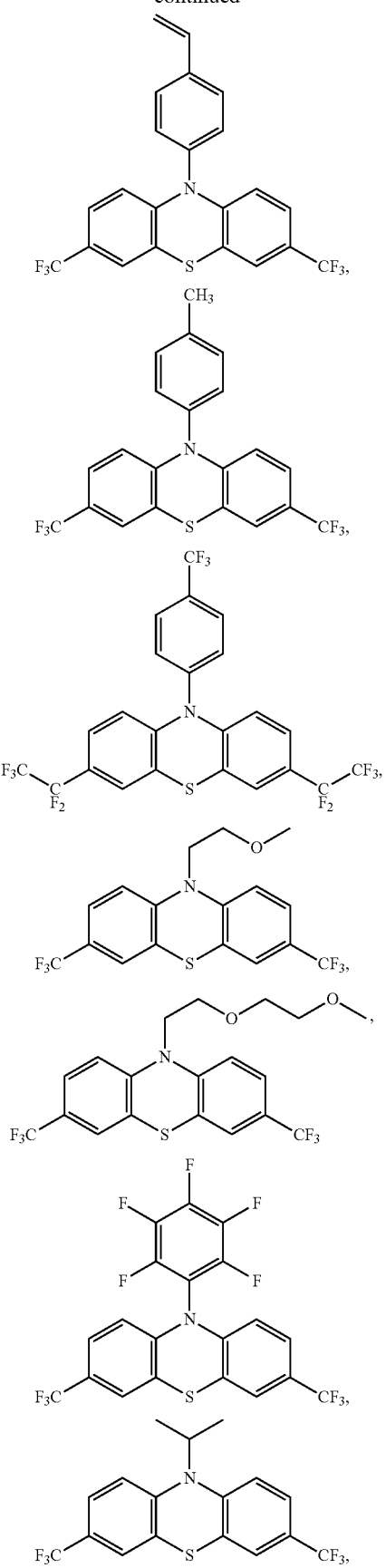

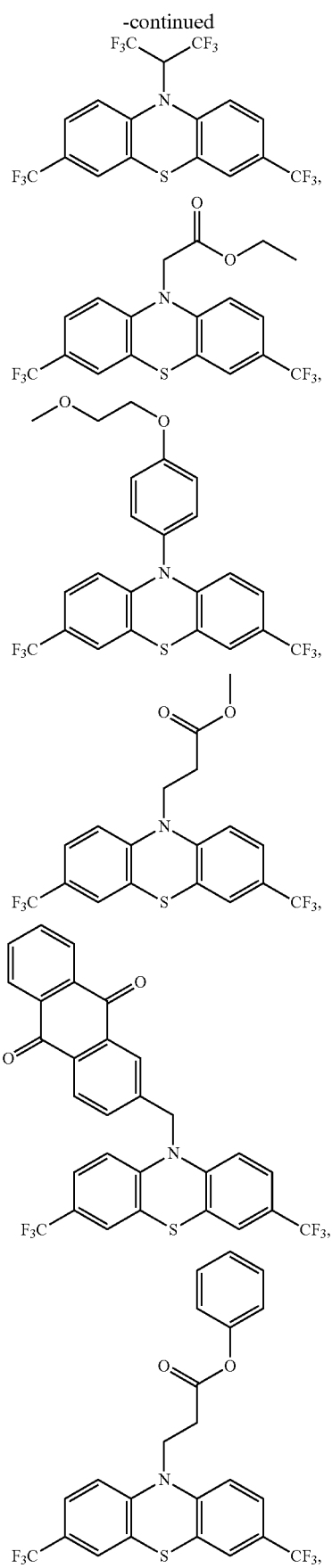
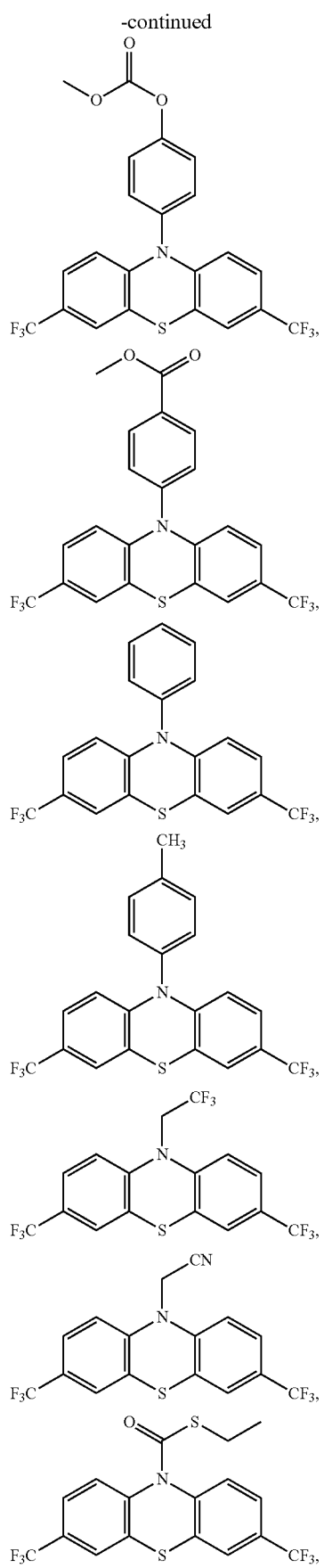

-continued

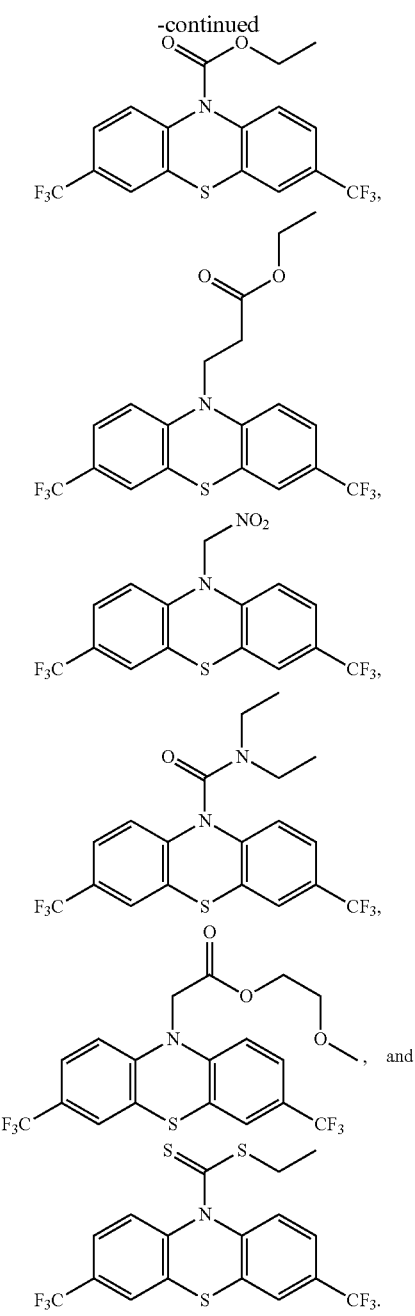

In some embodiments, the first and the second non-aqueous liquid electrolyte solutions are the same. In some embodiments, when the first and second non-aqueous liquid electrolyte solutions are the same, the solutions comprise a positive electrolyte and a negative electrolyte. In some of these embodiments, the positive electrolyte, or proton donor, and the negative electrolyte, or proton acceptor, is the same compound.

In some embodiments the present compounds include a BCF3EPT compound (shown below). The present compound exhibits superior solubility as a redox shuttle and can be stable for a relatively large number of overcharge cycles. Some embodiments of compounds can tolerate relatively high charging rates. Exemplary compounds can be stable neutral and oxidized (radical cation) states, exhibit relatively high oxidation potentials, and high solubility, and can increase capacity of non-aqueous all-organic redox flow batteries.

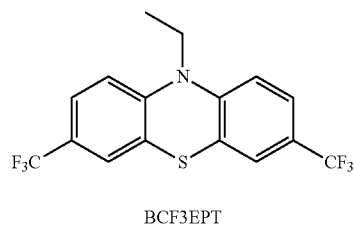 [SMILES: CCN1c2ccc(C(F)(F)F)cc2Sc2cc(C(F)(F)F)ccc21]

BCF3EPT

In some embodiments the compounds include the formula set forth below:

FORMULA I

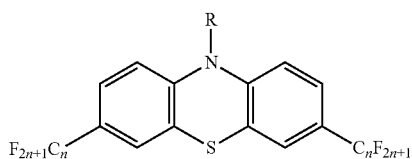

wherein R is selected from alkyl, aryl, alkylaryl, aloxyarul, alkylcarboxyl, aryl carbonyl, haloalkyl, perfluoroalkyl, glycols, haloaryl, vinyl, [please provide other polymerizable groups that would work well here], a negative electrolyte [please provide examples or a reference], and combinations thereof; wherein the carbonyl is not directly attached to the N, m is less than 25, and wherein each n is independently an integer from 1 to 6.

In some embodiments the present compounds include N-substituted phenothiazines with one or two strong electron withdrawing groups, including, for example, nitro, trifluoromethyl, cyano, trifluoroacetyl, and can include one of the following non-limiting formulas:

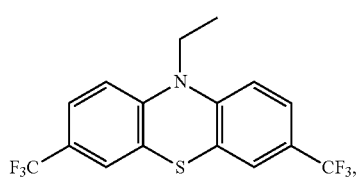

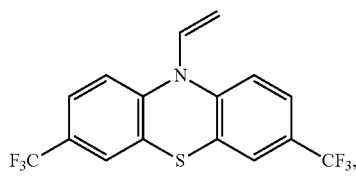

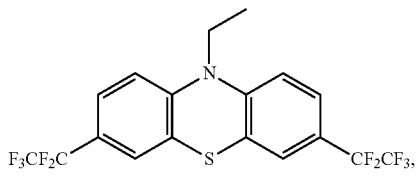

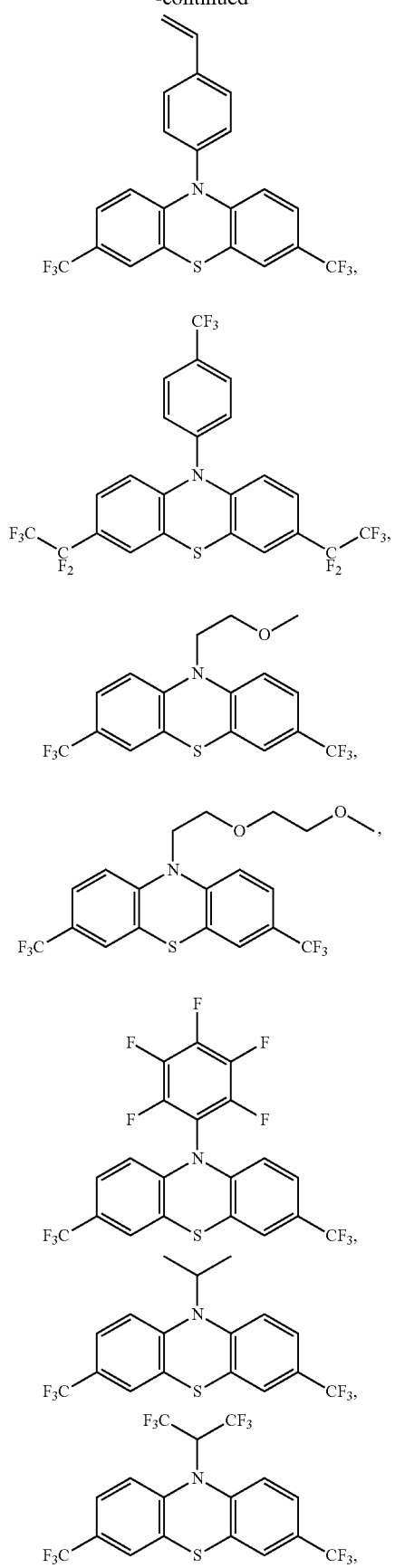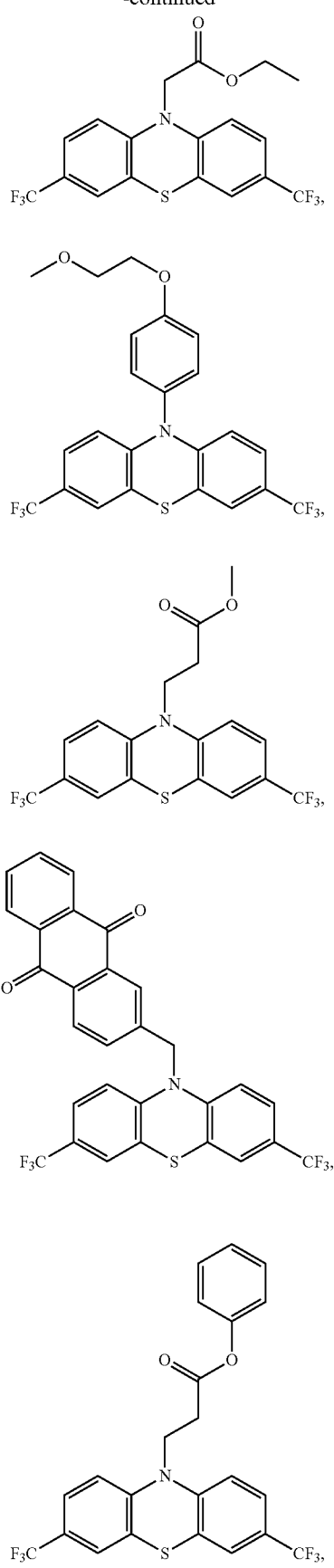

-continued
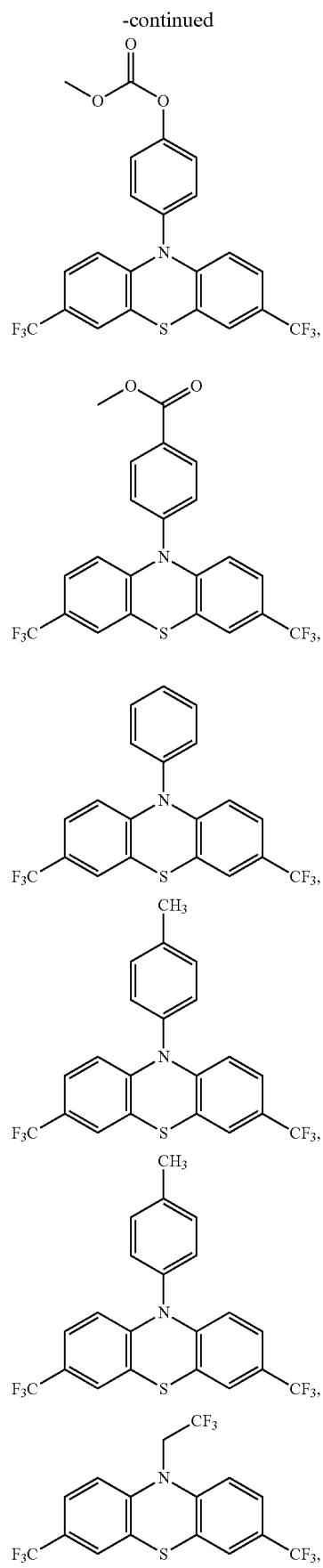
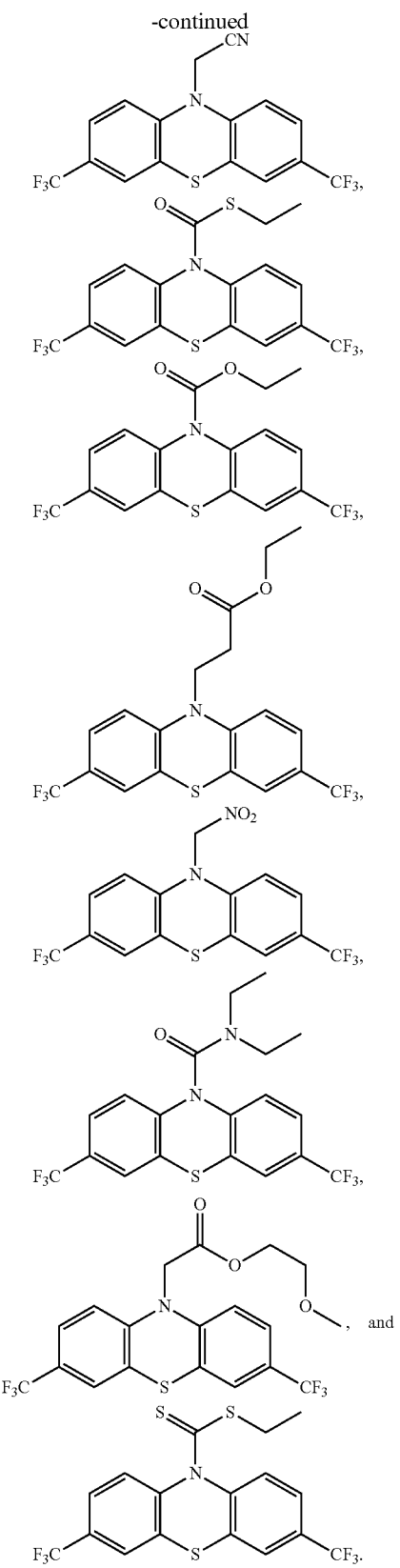
In some embodiments, the compound comprises both a negative electrolyte, or electron acceptor, and a positive electrolyte, or electron donor. In some embodiments, the electron acceptor is a quinone such as napthoquinone or a nitrogen-containing aromatic such as pyrazine or trimethylquinoxilane. In some embodiments, the electron acceptor of the compound is an anthroquinone. In some embodiments, the compound is:

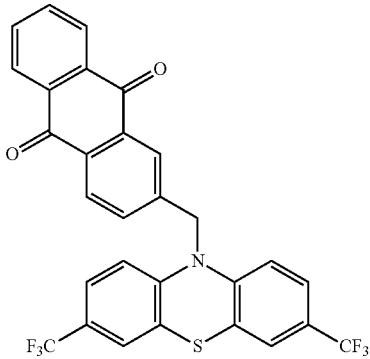 [SMILES: O=C1c2ccccc2C(=O)c2cc(CN3c4ccc(C(F)(F)F)cc4Sc4cc(C(F)(F)F)ccc43)ccc21]

The non-aqueous liquid electrolyte solution of the presently-disclosed non-aqueous redox flow battery comprises an organic solvent, which can be selected, for example, from a carbonate solvent, a nitrile, an ether, an aromatic compound, and an ester. Examples of appropriate carbonate solvents include, but are not limited to propylene carbonate, ethylene carbonate, ethyl methylcarbonate, diethylcarbonate, and dimethylcarbonate. Examples of appropriate nitriles include, but are not limited to acetonitrile, 1,4-dicyanobutane, 1,6-dicyanohexane. Examples of appropriate ethers include, but are not limited to diethylether, 1,4-dioxane, diethylene glycol diethyl ether, ethyl ether, and tetrahydrofuran. Examples of aromatic compounds include, but are not limited to, benzene, toluene, and 1,2-dichlorobenzene. An example of a glycol includes, but is not limited to, triethylene glycol, Examples of esters include, but are not limited to, ethyl acetate. Other solvents are described, for example, in R. M. Darling et al., Pathways to low cost electrochemical energy storage: a comparison of aqueous and nonaqueous flow batteries, Energy Environ, Sci., 2014, 7, 3459-3477, incorporated by reference in its entirety.

In some embodiments, the solvent is a polar solvent. Polar organic solvents include, but are not limited to, acetonitrile, acetone, tretahydrofurane, acetic acid, acetyl acetone, 2-aminoethanol, aniline, anisole, benzene, benzonitrile, benzyl alcohol, 1-butanol, 2-butanol, i-butanol, 2-butanone, t-butyl alcohol, carbon disulfide, carbon tetrachloride, chlorobenzene, chloroform, cyclohexane, cyclohexanol, cyclohexanone, di-n-butylphthalate, 1,1-dichloroethane, dichloroethane, diethylamine, diethylene glicol, diglyme, dimethoxyethane (glyme), N,N-dimethylaniline, dimethylformamide (DMF), dimethylphthalatem dimethylsulfoxide (DMSO), dioxane, ethanol, ether, ethyl acetate, ethyl acetoacetate, ethyl benzoate, ethylene glicol, heptane, hexane, methanol, methyl acetate, methyl t-butyl ether (MTBE) methylene chloride, 1-octanol, pentane, 1-pentanol, 2-pentanol, 3-pentanol, 2-pentanone, 3-pentanone, 1-propanol, 2-propanol, pyridine, tetrahydrofuran(THF), toluene and p-xylene.

In other embodiments, the non-aqueous liquid is an ionic liquid. When an ionic liquid is used in a non-aqueous system, this is preferably an inorganic salt made of the combination of cations including, but not limited thereto, ammonium, immidazolium, piperidinium, pyrrolidinium, phophosium and sulfonium cations with anions including, but not limited thereto, diethyl phosphate, bromide, iodide, chloride, methylsulfate, dodecylbenzenesulfonate, Trimethylpentyl)phosphinate, dicyanamide, decanoate, inflate, bis(trifluoromethylsulfonyl)imide, 1,1,2,2-tetrafluoroethanesulfonate, perfluorobutanesulfonate, hexafluorophosphates, tetrafluoroborates, sulphate, sulfonate, phosphate, thiocyanate, dicyanamide, acetate trifluoroacetate, nitrate, tetrachloroferrate, tetrathiocyanocobaltate and methylcarbonate.

The non-aqueous redox flow batteries of the presently disclosed invention include a semi-permeable separator. Non-limiting examples of suitable separator materials include sulfonated tetrafluoroethylene-based fluoropolymer-copolymers, such as NAFION® type ion exchange membranes, sulfonated poly(ether ether ketones), polysulfones, polyethylene, polypropylene, ethylene-propylene copolymers, polyimides, polyvinyldifluorides, and the like, which can be in the form of membranes, matrix-supported gels, sheets, films, or panels. Other suitable materials include porous ceramics, porous insulated metals, cation-conducting glasses, and zeolites. Other porous films, panels or mesh will be readily understood by those skilled in the art.

The compounds used in the non-aqueous redox flow battery has high solubility. In some embodiments, the compound has a solubility of about 0.5M or greater. In some embodiments, the compound has a solubility of about 1.0M or greater. In some embodiments, the compound has a solubility of about 2.0M or greater. In some embodiments, the compound has a solubility of about 3.0M or greater. In some embodiments, the compound has a solubility of about 4.0M or greater. In some embodiments, the compound has a solubility of about 5.0M or greater. In some embodiments, the compound has a solubility in the non-aqueous liquid electrolyte solution of about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 M. The high solubility of the compounds disclosed herein in conjunction with the non-aqueous redox flow battery provides a higher capacity battery that can be used in commercial applications.

In some embodiments, the non-aqueous electrolyte solution comprises a metal halide salt. Non-limiting examples of the metal halide salt include $LiBF_4$, $NaBF_4$, $LiPF_6$, $NaPF_6$, lithium bis(oxalato)borate, tetra-n-butylammonium hexafuorophosphate tetra-n-butylammonium bromide, tetra-n-butylammonium tetrafluoroborate.

In some embodiments, the metal halide salt comprises a cation such as, for example, $Li^+$ and $Na^+$. In some embodiments, the metal halide salt comprises anions such as, for example, $BE_4^-$, $PF_6^-$, $ClO_4^-$, $AsF_6^-$, $CF_3SO_3^-$, $N(SO_2CF_3)_2^-$, $N(SO_2CF_2CF_3)_2^-$, $B(C_2O_4)_2^-$, and $B_{12}X_6H_{(12-n)}^{2-}$, wherein X is a halogen.

The electrodes utilized according to the invention can include metal, a carbon material, or a combination thereof. Examples include platinum, copper, aluminum, nickel or stainless steel, acetylene black, carbon black, activated carbon, amorphous carbon, graphite, graphene, or a nanostructured carbon material, or a combination thereof. The electrode can be porous, fluted, or smooth.

In some instances the redox flow battery includes the redox flow battery shown in U.S. Patent Application Publication No. 2013/0224538 to Jansen et al., which is incorporated herein by this reference.

In some instances, the non-aqueous redox flow battery provides stability over about 500 cycles, 600 cycles, 700 cycles, 800 cycles, 900 cycles or 1000 cycles or more.

Terms have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting Examples. The following examples may include compilations of data that are representative of data gathered at various times during the course of development and experimentation related to the present invention.

EXAMPLES 3,7-bis(trifluoromethyl)-N-ethylphenothiazine (BCF3EPT, FIG. 1) is disclosed herein for use as a catholyte as a redox couple for a non-aqueous Redox Flow Battery. Its performance with 2,3,6-trimethyl quinoxaline (TMeQ, FIG. 1) as the anolyte was evaluated using a static Swagelok cell and is here compared to previously reported all-organic RFBs(23) containing 2,5-di-tert-butyl-1,4-bis(2-methoxyethoxy)benzene (DBBB, FIG. 1) as the catholyte and TMeQ as the anolyte.

The electrolyte used for cyclic voltammetry and battery fabrication was 0.2 M LiBF4 (98%, anhydrous, Acros Organics) in propylene carbonate (PC, 99.99%, BASF corporation). TMeQ (97%) was obtained from Alfa Aesar. BCF3EPT was synthesized as previously reported.(30) DBBB was synthesized according to the procedure reported by Zhang et al.31 with slight modifications. 2,5-Di-tert-butyl-1,4-hydroquinone (99%) was purchased from Acros Organics, and sodium hydride (95%) and 2-chloroethylmethyl ether (98%) were purchased from Sigma Aldrich Anhydrous N,N-dimethylformamide was purchased from Acros Organics. The MBraun argon-filled glovebox used for air- and water-sensitive experiments reported O2 levels≤0.6 ppm and H2O levels≤1.2 ppm.

Synthesis of DBBB 2,5-Di-tert-butyl-1,4-hydroquinone (2.5 g, 11 mmol) was added to anhydrous DMF (25 mL) in an oven-dried 100 mL round-bottomed flask under nitrogen. Sodium hydride (0.81 g, 34 mmol) was weighed in an argon-filled glovebox and added to a second oven-dried 100 mL round-bottomed flask containing a stir bar and capped with a septum. The flask was then removed from the glovebox and immersed in an ice-water bath under nitrogen. The suspension of 2,5-di-tert-butylhydroquinone in DMF was then gradually added to the flask containing sodium hydride, and the mixture was stirred for 20 min. 2-Chloroethyl methyl ether (2.1 mL, 22 mmol) was added dropwise, and the reaction flask was stirred overnight and allowed to warm to room temperature. The contents of the flask were then slowly poured into a cold solution of aqueous sodium bicarbonate and swirled, after which the organic product was extracted with ethyl acetate. The combined organic layers were dried over anhydrous magnesium sulfate, filtered to remove solids, and concentrated by rotary evaporation. The resulting crude product was purified by column chromatography (dichloromethane/hexanes, initially 1:1 and eventually increasing to 2:1) to yield the product in 45%. The product was crystallized from hexanes prior to incorporation into batteries. 1H NMR (400 MHz, CDCl3): δ/ppm 6.84 (s, 2H), 4.11 (t, J=5.2 Hz, 4H), 3.78 (t, J=5.2 Hz, 4H), 3.45 (s, 6H), 1.37 (s, 18 H); 13C NMR (100 MHz, CDCl3): δ/ppm 151.4, 136.7, 112.7, 71.8, 68.16, 59.3, 34.8, 30.1.

Solubility, Electrochemical, and UV-vis Measurements

To study electro-active species solubility in 0.2 M LiBF4 in PC, each compound was stirred for 1 h at room temperature at an initial concentration chosen based on prior experience with a similar electrolyte (1.2 M LiPF6 in EC/EMC); if crystals remained in solution, it was diluted as necessary. Electrochemical experiments were performed in an argon-filled glovebox at room temperature. Cyclic voltammetry (CV) measurements were performed in a three-electrode cell with a 3 mm diameter glassy carbon working electrode, Pt wire counter electrode, and Li foil reference electrode; voltammograms were taken of 0.2 M LiBF4 in PC containing 5 mM analyte using a CH Instruments 605E potentiostat. For UV-vis spectra of neutral compounds, catholytes were dissolved at 0.2 mM or 5 mM in 0.2 M LiBF4 in PC in glovebox and were removed in special optical glass cuvettes (Starna) after sealing with Teflon caps. The solutions were subsequently monitored for 5 h on an Agilent 8453 diode-array spectrometer.

Bulk electrolysis experiments were performed at 5 mM analyte in 0.2 M LiBF4 in PC with a Pt coiled-wire working electrode and a Li foil reference electrode, as well as a Pt wire counter electrode suspended in solution in a separate fitted glass tube. Electrolysis potentials were applied for 84 min in the glovebox, after which the solutions were diluted and removed from the glovebox in special optical glass cuvettes (Starna) sealed with Teflon caps. The solutions were subsequently monitored for 5 hours on an Agilent 8453 diode-array spectrometer.

Battery Cycling

Charge/discharge experiments were performed using a Swagelok cell cycled by a Maccor 4200 battery cycler. Nafion 117 (Aldrich, 1.27 cm2 geometric surface area) was used as the separator membrane between two graphite felt electrodes (Sigracell® GFA6, 0.71 cm2 geometric surface area). The graphite felt was vacuum dried at 80° C. overnight prior to use. The Nafion membrane was pretreated and soaked in a solution of 0.2 M LiBF4 in PC for several days prior to assembly of the Swagelok cell. The positive and negative graphite electrodes were soaked in solutions of catholyte and anolyte, respectively, in 0.2 M LiBF4 in PC for 4-5 h prior to use. The solutions contained 50 mM, 0.15 M, or 0.35 M of BCF3EPT in 0.2 M LiBF4; 50 mM, 0.15 M, or 0.35 M of TmeQ in 0.2 M LiBF4; or 50 mM or 0.15 M DBBB in 0.2 M LiBF4. All solutions were prepared in the glovebox at room temperature. When soaked, the foam electrodes absorb approximately 0.5 g of solution (range: 0.548 to 0.513 g). Each Swagelok cell was assembled in the argon-filled glovebox and was removed for cycling. The cells were cycled between 0.2 and 2.5 V at 0.1 mA.

Figures 2A, 2B:
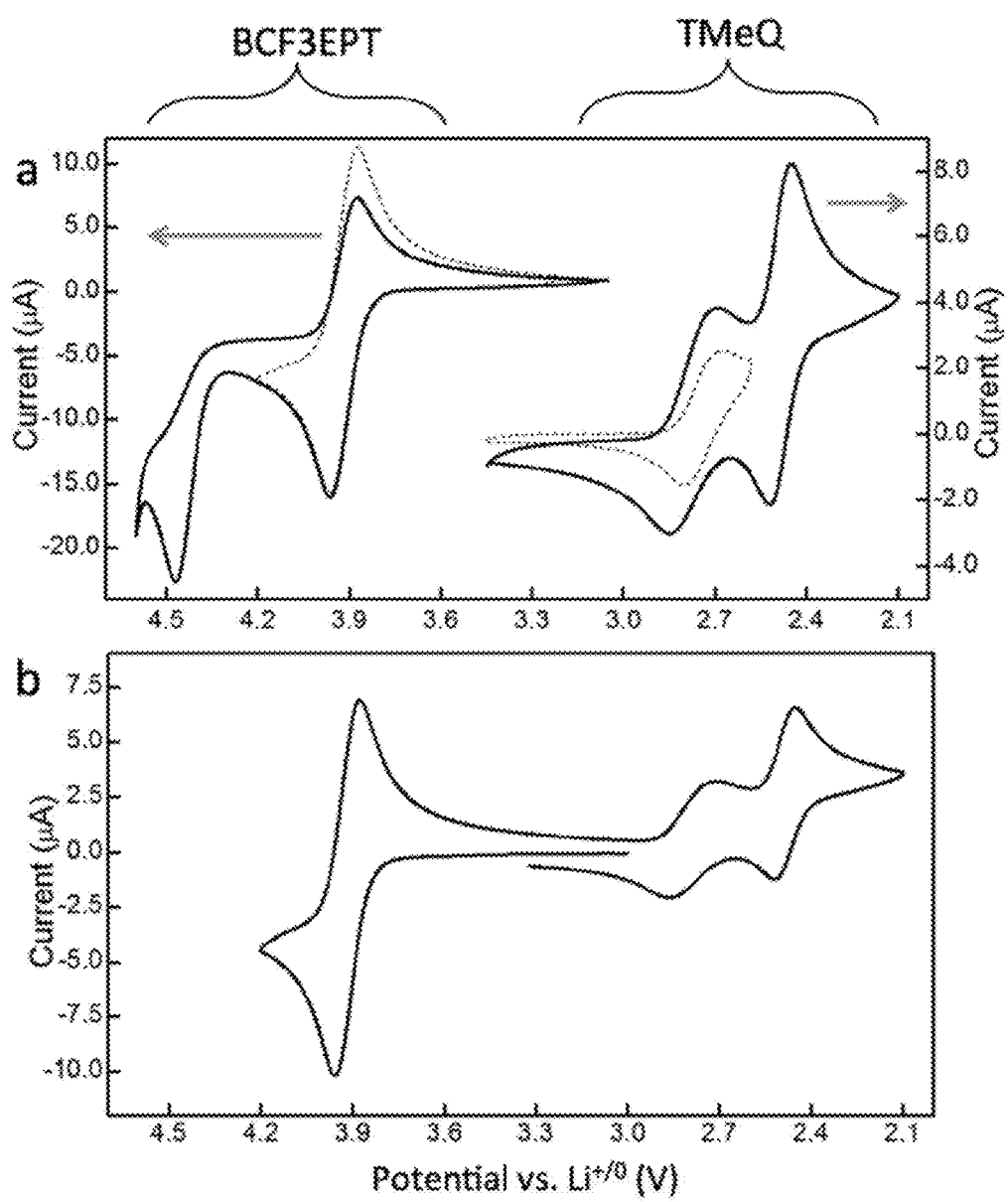
FIGS. 2A and 2B: Cyclic voltammograms of separate 5 mM BCF3EPT and 5 mM TMeQ solutions (a); and combined BCF3EPT and TMeQ at 5 mM each (b), all in 0.2 M $LiBF_4$ in PC and obtained at scan rates of 20 mV/s. Dashed lines show cycle to only one redox event.
Figure 6A:
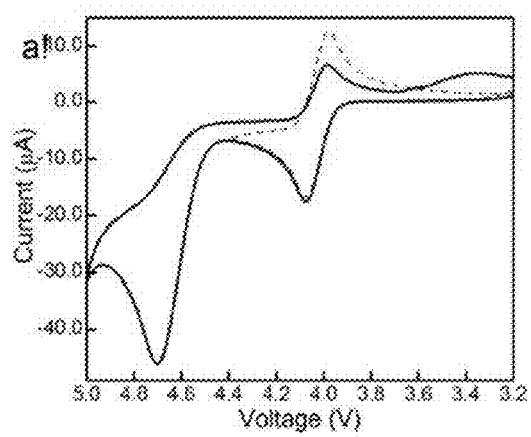
FIGS. 6A and 6B: Cyclic Voltammetry (CV) of 5 mM DBBB (a); and 1:1 mix DBBB and TMeQ (b) in 0.2 M $LiBF_4$ in Propylene Carbonate (PC).
Figure 6B:
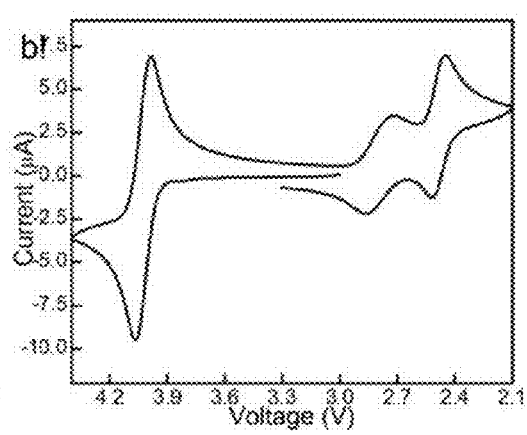

Cyclic voltammetry was used to characterize the electrochemical behavior of BCF3EPT and to characterize DBBB and TMeQ for comparison with reported data. The individual redox events for these electro-active materials can be used to estimate the open-circuit voltage (OCV) of an ORFB containing each catholyte-anolyte pair. $LiBF_4$ (0.2M) was used in propylene carbonate (PC) for these experiments to allow for direct comparison with the previously reported DBBB/TMeQ battery. The voltammograms of BCF3EPT show a reversible first oxidation at a potential of 3.9 V vs. $Li+/0$, which corresponds to generation of the radical cation, followed by an irreversible second oxidation at ca. 4.4 V vs. $Li+/0$ (FIG. 2a) corresponding to formation of the dication. Similar electrochemical behavior was observed for DBBB in LiBF4/PC, which showed a reversible first oxidation at 4.0 V vs. $Li+/0$ and an irreversible second oxidation at 4.7 V vs. $Li+/0$ (FIG. 6). No peaks corresponding to the reduction of the neutral compounds was observed during the anodic scans of BC3EPT and DBBB in this electrolyte. TMeQ showed two reversible redox events at potentials of 2.8 V and 2.5 V vs. $Li+/0$ (FIG. 2a), as were also observed by Brushett et al,(23) corresponding to the formation of the radical anion and the dianion, respectively. Voltammograms covering all reversible redox events of a 1:1 combination of BCF3EPT and TMeQ are shown in FIG. 2b. The equivalent voltammogram for DBBB and TMeQ is shown in FIG. 6b. Table 1 lists the half-wave oxidation and reduction potentials of the molecules studied. The redox potentials of BCF3EPT and DBBB are similar, thus it is contemplated that they will give similar cell voltages when coupled with TMeQ in an ORFB.

TABLE 1

List of half wave redox potentials for electro-active species obtained from cyclic voltammograms of solutions containing analyte at 5 mM in 0.2M $LiBF_4$ in PC with scan rates of 20 mV/s.

| Electro-active species | Low potential event vs. $Li^{+/0}$ (V) | High potential event vs. $Li^{+/0}$ (V) |
|---|---|---|
| BCF3EPT | 3.9 | 4.4[a] |
| DBBB | 4.0 | 4.7[a] |
| TMeQ | 2.5 | 2.8 |

Figures 3A, 3B:
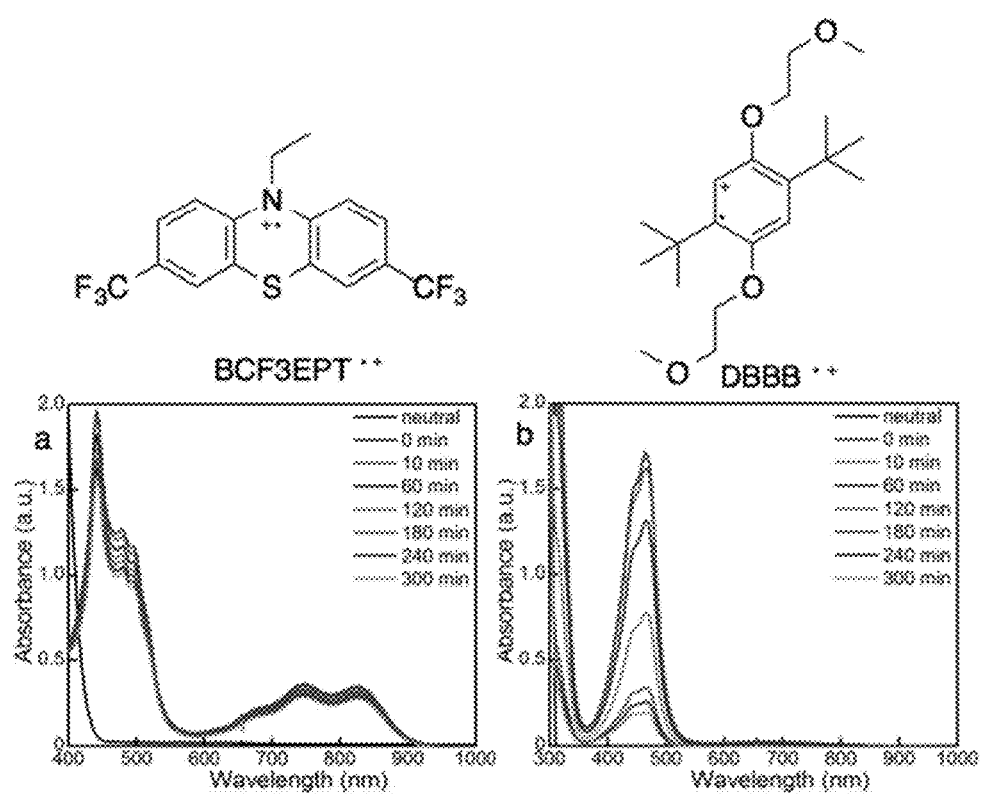
FIGS. 3A and 3B: UV-vis absorption spectra of radical cations of BCF3EPT (a) and DBBB (b) recorded at various times from 0 to 5 h after generation by bulk electrolysis at 5 mM in 0.2 M $LiBF_4$ in PC.
Figures 7A, 7B, 7C, 7D:
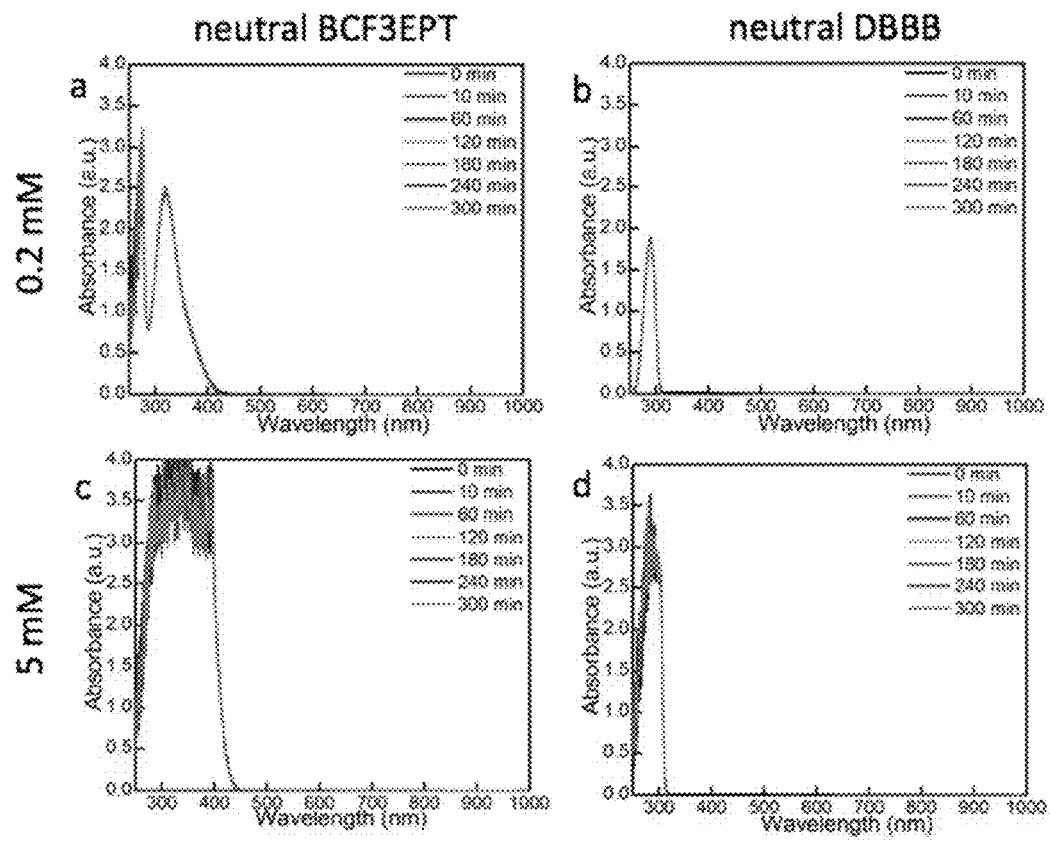
FIG. 7A-7D: UV-vis absorption spectra of BCF3EPT at 0.2 mM (a) and 5 mM (b) and DBBB at 0.2 mM (a) and 5 mM (b) in 0.2 M $LiBF_4$ in PC. Spectra are shown to 1000 nm to show that radical cations, which appear at lower wavelengths (see FIG. 2) does not form.
Figure 8:
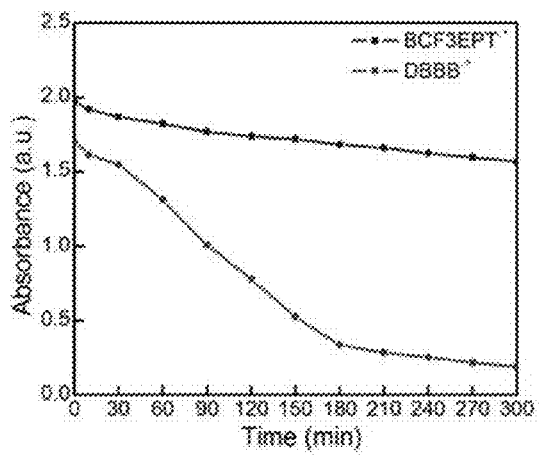
FIG. 8: Plot of original absorbance for the tallest peak in the UV-vis spectrum of radical cation of BCF3EPT and DBBB radical cation vs. time in 0.2 M $LiBF_4$ in PC from experiment in FIGS. 3A and 3B.

[a]irreversible oxidation potential calculated by estimating the position of the reverse wave and taking an average of the forward wave and estimate of reverse wave Although cyclic voltammetry can be used to identify impractical catholyte candidates if their first oxidation events are irreversible, reversibility over the short timescale represented by a voltammogram does not guarantee that a radical cation is stable enough to support a RFB over the long term. Additionally, a compound that is stable in ambient conditions may be sensitive to electrolyte components, as was previously observed for a phenothiazine derivative with a tert-butyl group at the N position.(31) To compare the stability of the neutral and radical-cation forms of BCF3EPT to those of DBBB, UV-vis spectra were collected for both of the oxidation states of both compounds in LiBF4/PC. The neutral compounds were measured at 0.2 mM and 5 mM in LiPF4/PC, and neither compound showed measurable signs of change over 5 h (FIG. 7). To simulate the charged species of each catholyte, the radical cation was generated by bulk electrolysis. UV-vis absorption spectra collected at regular time intervals over a 5 h period showed that the radical cation form of BCF3EPT was significantly more stable than the radical cation of DBBB in this electrolyte (FIG. 3). The spectra of BCF3EPT showed a relatively slow decay in absorption intensity, with ca. 80% of the original intensity remaining after 5 h (FIG. 8). By contrast, the absorption intensity of the DBBB radical cation decreased significantly within 2 h, and ca. 11% of the original signal remained after 5 h. This result is consistent with the higher stability of BCF3EPT observed relative to 1,4-bis(tert-butyl)-2,5-dimethoxybenzene (DDB), a compound similar in structure to DBBB, in 1.2 M LiPF6 in ethylene carbonate/ethyl methylcarbonate (EC/EMC)29 and supports BCF3EPT will be a more suitable catholyte for non-aqueous RFBs.

To study the behavior of the new catholyte BCF3EPT relative to DBBB, a set of batteries with the same concentration of electro-active species as the reported DBBB/TMeQ battery (0.05 M), as well as with the highest concentration possible for all three species, were identified for comparison. The maximum solubilities for DBBB, TMeQ and BCF3EPT in 0.2 M LiBF4 in PC were ca. 0.18 M, 0.37 M, and 1.2 M, respectively. Hence stationary RFBs were fabricated at 0.05 M and 0.15 M concentrations for both sets of redox couples. Batteries were also fabricated at the highest concentration possible for BCF3EPT and TMeQ (0.35 M), beyond that which was possible for DBBB. By this measure, two sets of batteries were able to be tested at the same concentrations, including one near the limiting concentration of DBBB, and a third that allowed for analysis of a battery near the solubility limit of TMeQ.

Figures 4A, 4B, 4C, 4D, 4E, 4F:
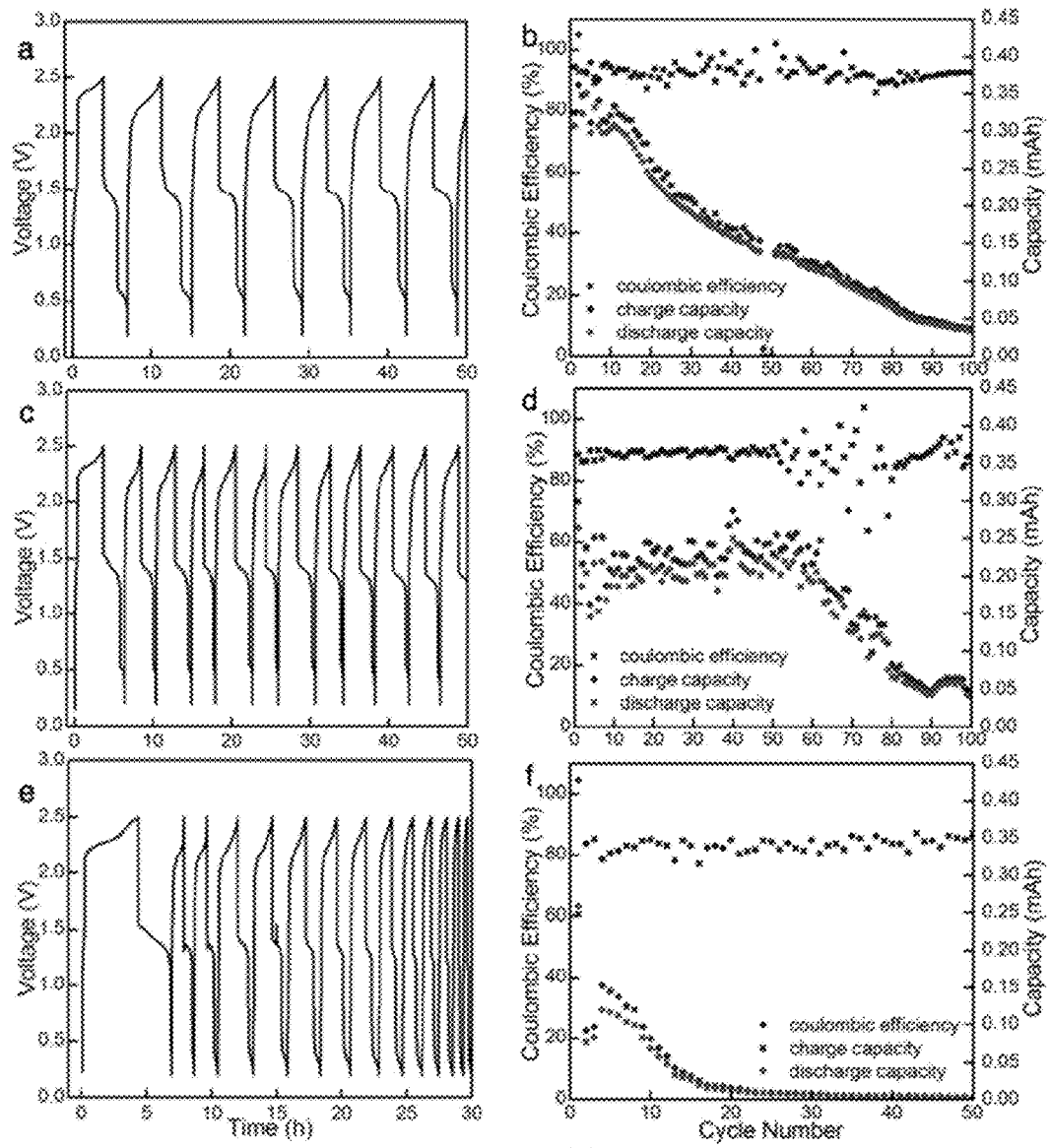
FIG. 4A-4F: Potential vs. time profile (first 50 hours) and capacity and coulombic efficiency vs. cycle number of a Swagelok cell containing BCF3EPT as the catholyte and TMeQ as the anolyte in 0.2 M $LiBF_4$ in PC at 0.05 M (a,b); 0.15 M (c,d); and 0.35 M (e,f) electro-active material.
Figure 5:
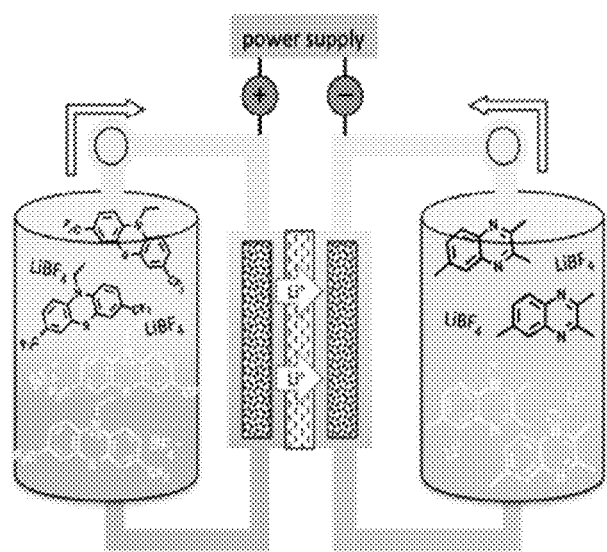
FIG. 5: Schematic of electro-active materials evaluated in stationary mimics of non-aqueous redox flow batteries.
Figures 9A, 9B, 9C, 9D:
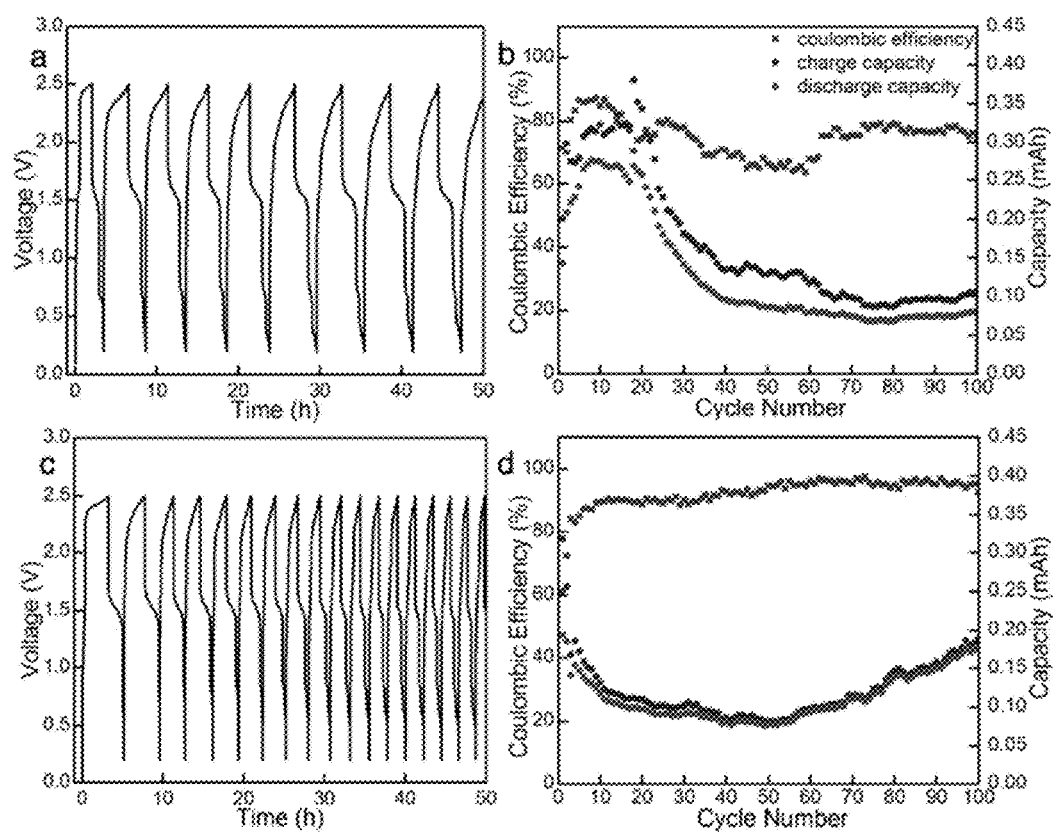
FIG. 9A-9D: Potential vs. time profile (first 50 hours) and capacity and coulombic efficiency vs. cycle number of a Swagelok cell containing DBBB as catholyte and TMeQ as anolyte in 0.2 M $LiBF_4$ in PC at 0.05 M (a, b); and 0.15 M (c, d) in 0.2 M $LiBF_4$ in PC.

The electrochemical cycling performance of Swagelok cells was analyzed by constant-current charging and discharging for BCF3EPT-TMeQ (FIG. 4) and DBBB-TMeQ (FIG. 9) cells at the aforementioned concentrations. FIG. 4A shows the performance of a Swagelok cell containing BCF3EPT and TMeQ at 0.05 M. During the first charging cycle, the cell showed a low voltage shoulder at 1.2-1.5 V and high voltage plateau at 2.2-2.4 V. During discharge, the cell plateaus were observed at 1.6-1.3 V and 0.6-0.4 V. The disparity between plateau voltages during charge and discharge cycles may arise from overpotential losses occurring in the cell, most likely due to concentration polarization from the static electrolyte. After two cycles, the cell transitioned to stable charging from 1.5-2.4 V and discharging from 1.5-1.3 V with a charging capacity of 0.67 mAh/g and a discharging capacity of 0.62 mAh/g. The coulombic efficiency at this concentration stabilized at ~92% for the BCF3EPT-TMeQ cell, whereas the capacities continued to decay over subsequent cycles. This cell lost essentially all of its capacity in 100 cycles (FIG. 4B). Similar behavior was observed for the DBBB-TMeQ Swagelok cell (FIGS. 9A and 9B), consistent with the results of Brushett et al. 23 For BCF3EPT-TMeQ cells containing 0.15 M electro-active species, stable performance was observed through about 60 cycles with average charging and discharging capacities of 0.44 and 0.37 mAh/g, respectively, and a coulombic efficiency of ca. 89%, which compares favorably to previous reports for non-aqueous systems. While the efficiencies remained between 80 and 90% for the equivalent 0.15 M DBBB-TMeQ, the capacities declined through the first 50 cycles (FIGS. 9C and 9D). The BCFEPT-TMeQ batteries containing 0.35 M electro-active material showed rapid decline in capacity, with capacities almost zero after 20 cycles (FIGS. 4E and 4F).

A visible color change in the lithiated Nafion membrane from clear to dark brown was observed in all of the Swagelok cells that were opened after cycling, independent of concentration and catholyte used. No visible color change occurred upon soaking Nafion membrane in freshly prepared electrolyte solutions over several days in the glovebox (i.e., when not subjected to electrochemical cycling). It is therefore likely that the Nafion membrane is reacting with one or both of the electro-active compounds in their neutral or charged forms, which not only reduces capacity but possibly blocks membrane pores. While it has been used in non-aqueous RFBs,(37) Nafion membranes were designed for proton crossover in aqueous systems and have not been well studied for Li+ exchange with organic solvents. In the batteries, crossover of the organic compounds through the membrane was observed via NMR analysis of the solutions on both sides of the membrane. NMR spectra of both electrolytes showed contamination of catholyte on the anolyte side and vice versa. Also, both BCF3EPT and DBBB can undergo irreversible second oxidations, so if the dication of either catholyte is formed through a second oxidation during charging, the charged species may react with the electrolyte or cell components, reducing overall capacity. The radical anion or dianion of the anolyte may similarly undergo unfavorable side reactions leading to capacity loss; however, UV-vis spectra of the radical anion of TMeQ do not show clear peaks that are distinguishable from the neutral form, preventing a comparable analysis of stability.

BCF3EPT is an example of compounds of the present invention for all-organic RFBs, demonstrated through the fabrication and testing of a stationary Swagelok battery containing a TMeQ anolyte. Stationary versions of flow batteries were fabricated with concentrations of catholyte and anolyte from 0.05 M to 0.35 M. The batteries containing 0.15 M electro-active material retained their capacity through the largest number of cycles, ca. 60, before fading occurred. Results compared to a dialkoxybenzene-based derivative as the catholyte show markedly improved stability of the radical cation form, and combined with the higher solubility of BCF3EPT, this compound is contemplated to be a promising catholyte, more promising than previously identified compounds, for non-aqueous RFBs containing organic electro-active materials.

Comparing Phenothiazine Derivatives.

Figure 10:
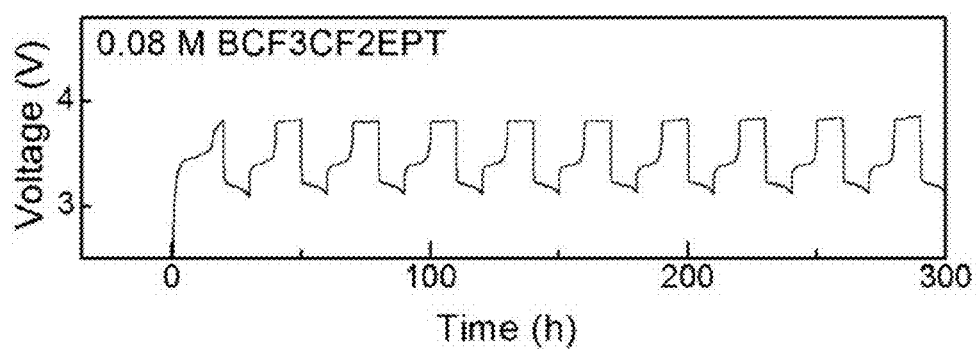
FIG. 10: Overcharge results for BCF3CF2EPT at 0.08M concentration.
Figure 11:
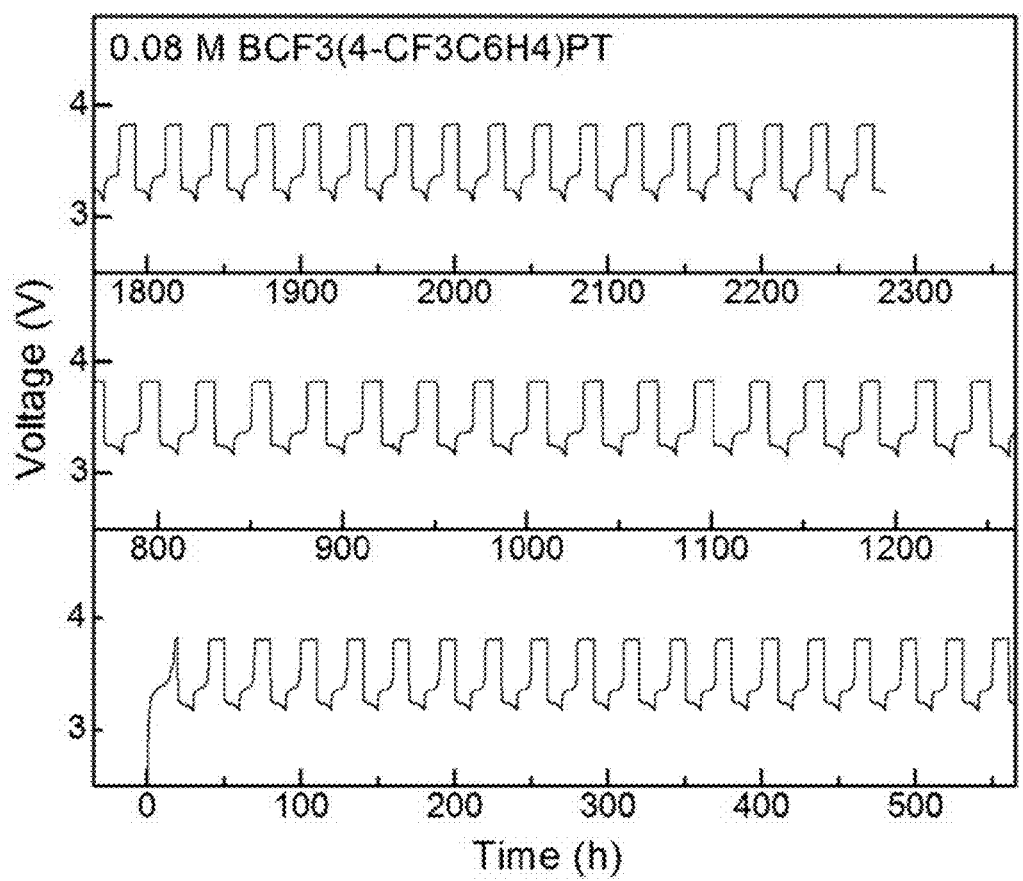
FIG. 11: Overcharge data for BCF3(4-CH3-C6H4)PT at 0.08M concentration.

Table 2 includes a compilation of data related to phenothiazine derivatives overcharge data of phenothiazine compounds as well as whether the compounds are practical for use in redox flow batteries. Such data includes the results for BCF3CF2EPT and BCF3(4-CH3-C6H4)PT, as set forth in FIGS. 10 and 11. Some phenothiazine derivatives have solubility and stability sufficient for overcharge protection, they are not sufficiently soluble to be practical for redox flow applications. As exemplified in Table 2, EPT and DClEPT are practical for overcharge protection but are not practical for redox flow.

TABLE 2

| Phenothiazine Derivative | Stability | Solubility | Quantitative Measure of Overcharge Protection (Redox Shuttle) Performance | Practical for Overcharge Protection? | Quantitative Measure of Redox Flow Performance | Practical for Redox Flow? |
| --- | --- | --- | --- | --- | --- | --- |
| BCF3EPT | high | 1.5-2.0M | ~250 cycles of 100% overcharge at ca. 3.8 V | Yes, because sufficiently stable to enable extensive overcharge protection. | In half cells, >250 charge/discharge cycles have completed to date with >99% coulombic efficiency | Yes, because sufficiently stable to lead to extensive cycles before capacity fade and is sufficiently soluble for practical use. |
| BCF3CF2EPT | High | TBD | >10 cycles at 100% overcharge (testing in progress) | Yes, because sufficiently stable to enable extensive overcharge protection. | TBD | Yes, (contemplated) because sufficiently stable and sufficiently soluble. |
| BCF3(4-CF3C6H4)PT | High | TBD | >70 cycles at 100% overcharge (testing in progress) | Yes, because sufficiently stable to enable extensive overcharge protection. | TBD | Yes, (contemplated) because sufficiently stable and sufficiently soluble. |
| PT | Low | 0.1M | 2-3 cycles | No, because insufficiently stable. | N/A | No, because it is insufficiently stable and is insufficiently soluble. |
| EPT | High | 0.1M | 65-160 cycles | Yes, because sufficiently stable. | N/A | No, because it is insufficiently soluble. |
| DClEPT | High | 0.1M | 19-37 cycles | | N/A | No, because it is insufficiently soluble. |
| MPT | high | 0.1M | 5 | No, although the neutral compound is | N/A | No, because it is insufficiently soluble. |

TABLE 2-continued

| Phenothiazine Derivative | Stability | Solubility | Quantitative Measure of Overcharge Protection (Redox Shuttle) Performance | Practical for Overcharge Protection? | Quantitative Measure of Redox Flow Performance | Practical for Redox Flow? |
| --- | --- | --- | --- | --- | --- | --- |
| DBrEPT | high | 0.1M | 2-5 | sufficiently stable, the radical cation (oxidized species) is insufficiently stable. No, it is subject to reduction at the anode and forms an unstable radical anion. | N/A | No, because it is insufficiently soluble. |
| DNO2EPT | TBD | Low | 0 | No, they are insufficiently soluble and cannot be evaluated. | N/A | No, because they are insufficiently soluble. |
| DCNEPT | high | low | 0-1 | | N/A | |

Table 2 provides a compilation of data from several sources. The data includes overcharge data at 100% overcharge for EPT, DBrEPT, DClEPT, BCF3EPT and DCNEPT from Ergun, et al. Chem. Comm., 2014, 50, 5339-5341. (30) Overcharge data at constant overcharge for EPT and BCF3EPT is derived from the studies described in Kaur et al., J. Materials Chemistry A, 2014, 2, 18190-18193. (29) Overcharge data at 100% overcharge for PT, MPT and EPT provided in Table 2 was derived from studies described in Narayana et al. ChemPhysChem, 2015, 16, 1179-1189. (32) Overcharge results for BCF3CF2EPT and BCF3(4-CF3C6H4)PT are provided in FIGS. 10 and 11, respectively.

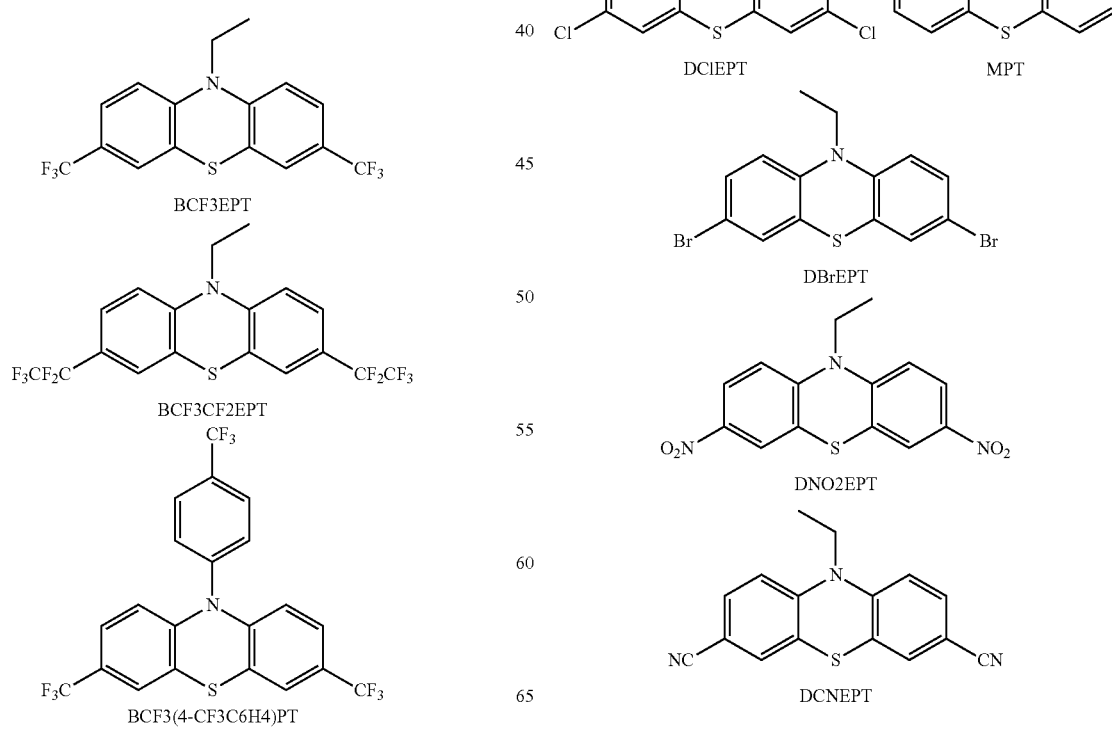

Half-cell Testing of Electrolytes for Non-aqueous Redox Flow Batteries

In the following study, the electrolyte used for battery fabrication was 1.0 M $LiBF_4$ (98%, anhydrous, Acros Organics) in propylene carbonate (PC, 99.99%, BASF corporation). The non-aqueous electrolyte preparation and coin cell assembly were completed inside MBraun glove box filled with argon with moisture and oxygen content less than 0.1 ppm. The cell was assembled with graphite felt (Sigracell®) soaked with a solution of catholyte as a working electrode and lithium foil as a counter as well as a reference electrode, sandwiched around a lithiated nafion membrane. The whole assembly was sealed in the glove box.

Figure 12A:
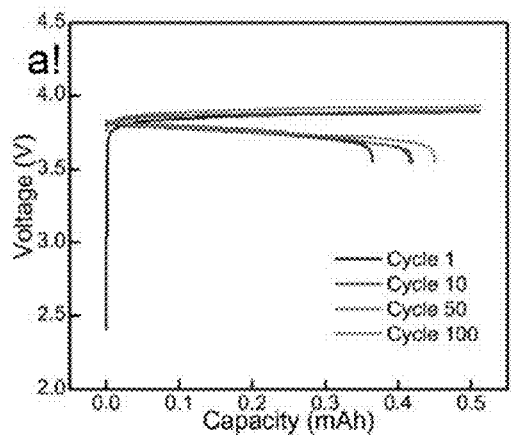
FIGS. 12A and 12B: The electrochemical performance of a coin cell with 0.25 M BCF3EPT in 1.0 M $LiBF_4$ in PC solution as a positive electrolyte and lithium metal as a negative electrode: (a) Cell voltage profile vs. capacity during a charge-discharge process; and (b) charge and discharge capacity as a function of cycle number.
Figure 12B:
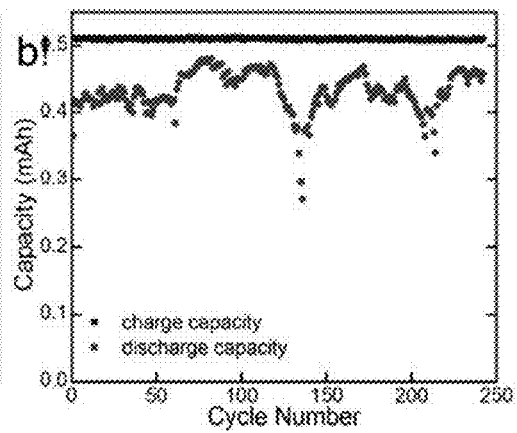
Figure 13:
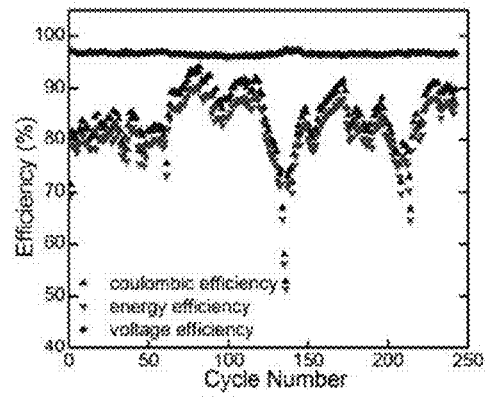
FIG. 13: Coulombic, energy and voltage efficiencies as a function of cycle number of a coin cell with 0.25 M BCF3EPT in 1.0 M $LiBF_4$ in PC solution as a positive electrolyte and lithium metal as a negative electrode.

In this study, half-cell testing is used as a screening technique to study electro-active materials for use as catholyte and/or anolyte in non-aqueous redox flow batteries. The optimization of half-cell testing was performed with BCF3EPT. Various separator membranes have been tested and the optimal procedure involved the use of lithiated nafion membrane as a separator between the felt and Li-foil electrode. The electrochemical cycling performance of BCF3EPT (FIGS. 12A and 12B) was evaluated using a constant-current method on a battery cycler (Maccor) using a static coin cell. The coin cell was cycled between 3.5 V and 4.2 V at a constant current of 0.1 mA. The two voltage plateaus (FIG. 12A) observed in the cell voltage profile during charge and discharge processes corroborate well with the cyclic voltammetry of BCF3EPT. The crossover of radical cation form of BCF3EPT through the nafion membrane was observed, which may be responsible for lower discharge capacities during each cycle. However, the charge capacity stays unchanged for more than 250 cycles, suggesting high electrochemical stability of BCF3EPT. BCF3EPT has a stable radical cation compared to other dimethoxy benzene deivatives. (29) FIG. 13 shows the various efficiencies for BCF3EPT coin cell, with coulombic and energy efficiencies between 80-90% for these 250 cycles. The voltage efficiency was stabilized at ca. 97%.

Throughout this document, various references are mentioned. All such references are incorporated herein by reference, including the references in the following list:

REFERENCES

1. Z. Yang, J. Zhang, M. C. W. Kintner-Meyer, X. Lu, D. Choi, J. P. Lemmon and J. Liu, *Chemical Reviews*, 2011, 111, 3577-3613.
2. J. Liu, J.-G. Zhang, Z. Yang, J. P. Lemmon, C. Imhoff, G. L. Graff, L. Li, J. Hu, C. Wang, J. Xiao, G. Xia, V. V. Viswanathan, S. Baskaran, V. Sprenkle, X. Li, Y. Shao and B. Schwenzer, *Advanced Functional Materials*, 2013, 23, 929-946.
3. R. M. Darling, K. G. Gallagher, J. A. Kowalski, S. Ha and F. R. Brushett, *Energy Environ. Sci.*, 2014, 7, 3459-3477.
4. M. Kinter-Myer, *PNNL Report*, 2012.
5. B. Dunn, H. Kamath and J. M. Tarascon, *Science*, 2011, 334, 928-935.
6. K. B. Hueso, M. Armand and T. Rojo, *Energy & Environmental Science*, 2013, 6, 734-749.
7. A. Parasuraman, T. M. Lim, C. Menictas and M. Skyllas-Kazacos, *Electrochimica Acta*, 2013, 101, 27-40.
8. P. Leung, X. Li, C. Ponce de Leon, L. Berlouis, C. T. J. Low and F. C. Walsh, *RSC Advances*, 2012, 2, 10125-10156.
9. M. Skyllas-Kazacos, M. H. Chakrabarti, S. A. Hajimolana, F. S. Mjalli and M. Saleem, *J. Electrochem. Soc.*, 2011, 158, R55-R79.
10. H. Kamath, S. Rajagopalan and M. Swillenberg, *Vanadium Redox Flow Batteries: An In-Depth Analysis*, EPRI, Palo Alto, Calif., 2007.
11. K. Xu, *Chem. Rev.,* 2004, 104, 4303-4417.
12. Y. Matsuda, K. Tanaka, M. Okada, Y. Takasu, M. Morita and T. Matsumura-Inoue, *J Appl Electrochem*, 1988, 18, 909-914.
13. T. Yamamura, Y. Shiokawa, H. Yamana and H. Moriyama, *Electrochimica Acta,* 2002, 48, 43-50.
14. C. H. Bae, E. P. L. Roberts and R. A. W. Dryfe, *Electrochimica Acta,* 2002, 48, 279-287.
15. M. H. Chakrabarti, R. A. W. Dryfe and E. P. L. Roberts, *Electrochimica Acta,* 2007, 52, 2189-2195.
16. Q. Liu, A. E. S. Sleightholme, A. A. Shinkle, Y. Li and L. T. Thompson, *Electrochemistry Communications,* 2009, 11, 2312-2315.
17. Q. Liu, A. A. Shinkle, Y. Li, C. W. Monroe, L. T. Thompson and A. E. S. Sleightholme, *Electrochemistry Communications,* 2010, 12, 1634-1637.
18. M. H. Chakrabarti, E. P. L. Roberts, C. Bae and M. Saleem, *Energy Conversion and Management,* 2011, 52, 2501-2508.
19. A. E. S. Sleightholme, A. A. Shinkle, Q. Liu, Y. Li, C. W. Monroe and L. T. Thompson, *Journal of Power Sources,* 2011, 196, 5742-5745.
20. T. Herr, P. Fischer, J. Tübke, K. Pinkwart and P. Elsner, *Journal of Power Sources,* 2014, 265, 317-324.
21. Z. Li, S. Li, S. Liu, K. Huang, D. Fang, F. Wang and S. Peng, *Electrochemical and Solid-State Letters,* 2011, 14, A171-A173.
22. W. Wang, W. Xu, L. Cosimbescu, D. Choi, L. Li and Z. Yang, *Chemical Communications,* 2012, 48, 6669-6671.
23. F. R. Brushett, J. T. Vaughey and A. N. Jansen, *Advanced Energy Materials,* 2012, 2, 1390-1396.
24. L. Su, M. Ferrandon, J. A. Kowalski, J. T. Vaughey and F. R. Brushett, *J. Electrochem. Soc.,* 2014, 161, A1905-A1914.
25. J. Huang, L. Cheng, R. S. Assary, P. Wang, Z. Xue, A. K. Burrell, L. A. Curtiss and L. Zhang, *Advanced Energy Materials,* 2014, n/a-n/a.
26. S. Hamelet, D. Larcher, L. Dupont and J.-M. Tarascon, *Journal of The Electrochemical Society,* 2013, 160, A516-A520.
27. S. H. Oh, C. W. Lee, D. H. Chun, J. D. Jeon, J. Shim, K. H. Shin and J. H. Yang, *J. Mat.* Chem. A, 2014.
28. R. Surendran Assary, L. A. Curtiss and F. R. Brushett, *RSC Advances,* 2014.
29. A. P. Kaur, S. Ergun, C. F. Elliott and S. A. Odom, *J. Mat. Chem. A,* 2014, 2, 18190-18193.
30. S. Ergun, C. F. Elliott, A. P. Kaur, S. R. Parkin and S. A. Odom, *Chem. Commun.,* 2014, 50, 5339-5341.
31. L. Zhang, Z. Zhang, P. C. Redfern, L. A. Curtiss and K. Amine, *Energy Environ. Sci.,* 2012, 5, 8204-8207.
32. K. A. Narayana, M. D. Casselman, C. F. Elliott, S. Ergun, S. R. Parkin, C. Risko and S. A. Odom, *ChemPhysChem,* 2015, 16, 1179-1189.
33. M. D. Casselman, A. P. Kaur, K. A. Narayana, C. F. Elliott, C. Risko and S. A. Odom, *manuscript submitted Nov.* 12, 2014.
34. S. A. Odom, S. Ergun, P. P. Poudel and S. R. Parkin, *Energy Environ. Sci.,* 2014, 7, 760-767.
35. S. Ergun, C. F. Elliott, A. P. Kaur, S. R. Parkin and S. A. Odom, *J. Phys. Chem. C,* 2014, 118, 14824-14832.
36. S.-H. Shin, S.-H. Yun and S.-H. Moon, *RSC Advances,* 2013, 3, 9095-9116.
37. T. Nagaura and K. Tozawa, Prog. Batteries Sol. Cells, 1990, 9, 209.

38. E. Stura and C. Nicolini, Anal. Chim. Acta, 2006, 568, 57-64.
39. M. Armand and J. M. Tarascon, Nature, 2008, 451, 652-657.
40. D. Belov and M.-H. Yang, J Solid State Electrochem, 2008, 12, 885-894.
41. R. A. Leising, M. J. Palazzo, E. S. Takeuchi and K. J. Takeuchi, Journal of Power Sources, 2001, 97-98, 681-683.
42. Z. Chen, Y. Qin and K. Amine, Electrochimica Acta, 2009, 54, 5605-5613.
43. T. J. Richardson and P. N. Ross, Journal of The Electrochemical Society, 1996, 143, 3992-3996.
44. A. J. Bard and L. R. Faulkner, Electrochemical methods: fundamentals and applications, Wiley, 1980.
45. J. R. Dahn, J. W. Jiang, L. M. Moshurchak, M. D. Fleischauer, C. Buhrmester and L. J. Krause, Journal of the Electrochemical Society, 2005, 152, A1283-A1289.

All publications, patents, and patent applications mentioned in this specification are herein incorporated by reference to the same extent as if each individual publication, patent, or patent application was specifically and individually indicated to be incorporated by reference It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A positive cell comprising a cathode and a compound according to the formula:

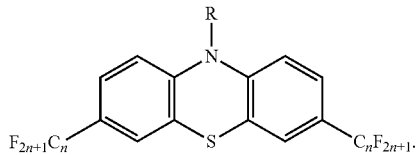

wherein R is selected from alkyl, aryl, alkylaryl, alkoxyaryl, alkylcarboxyl, aryl carbonyl, haloalkyl, perfluoroalkyl, glycol, haloaryl, a negative electrolyte, and a polymer; and wherein each n is independently an integer from 1 to 6.

2. A non-aqueous redox flow battery comprising:
a negative electrode immersed in a first non-aqueous liquid electrolyte solution;
a positive electrode immersed in a second non-aqueous liquid electrolyte solution; and
a semi-permeable separator interposed between the negative and positive electrodes;
wherein the second the non-aqueous liquid electrolyte solution comprises a compound of the formula:

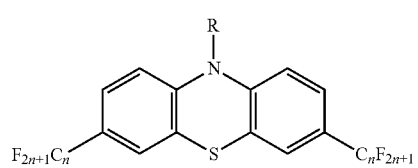

wherein R is selected from alkyl, aryl, alkylaryl, alkoxyaryl, alkylcarboxyl, aryl carbonyl, haloalkyl, perfluoroalkyl, glycols, haloaryl, a negative electrolyte, and a polymer; and wherein each n is independently an integer from 1 to 6.

3. The battery of claim 2, wherein the compound has a solubility greater than about 0.5 M.

4. The battery of claim 2, wherein the compound is selected from the group consisting of:

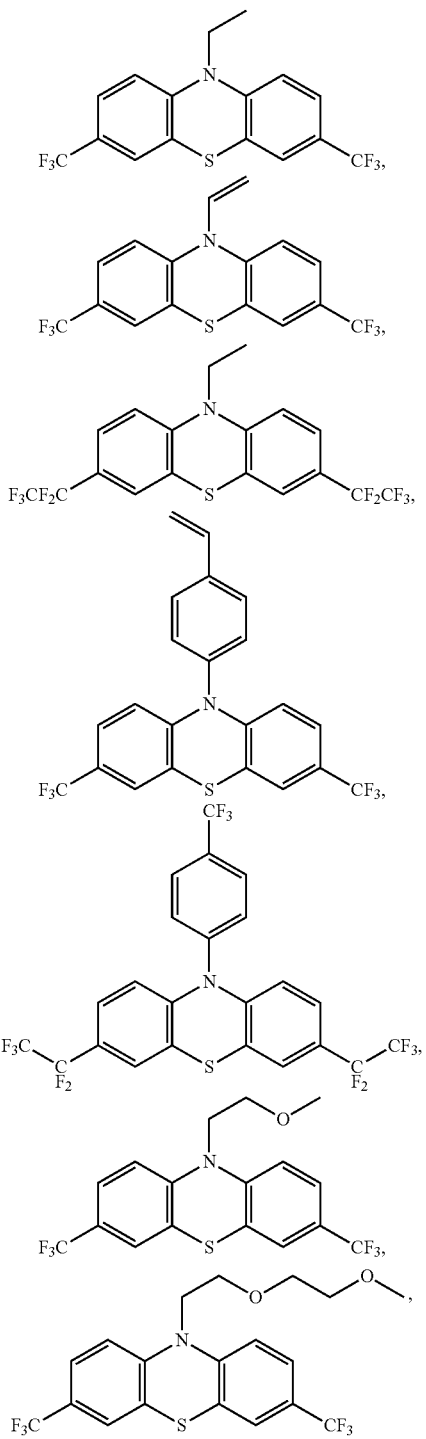

37
-continued

38
-continued

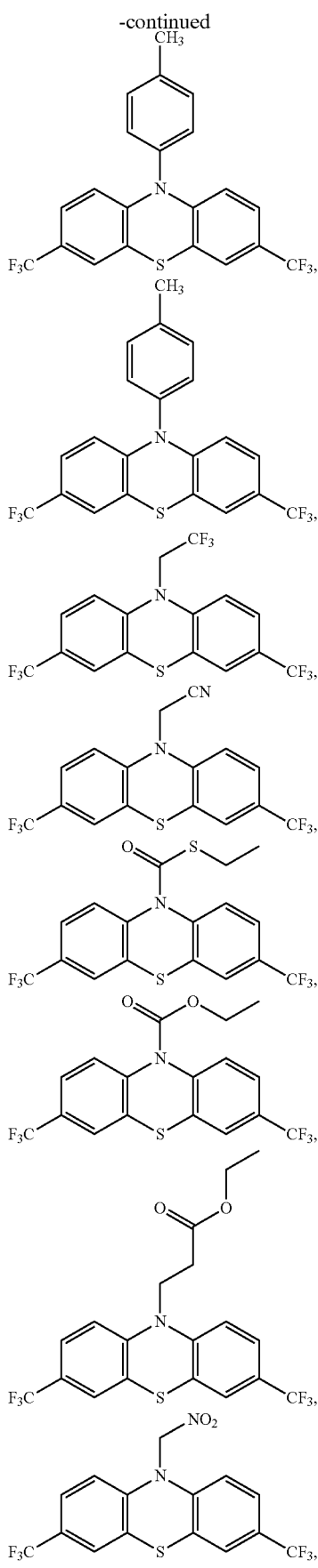

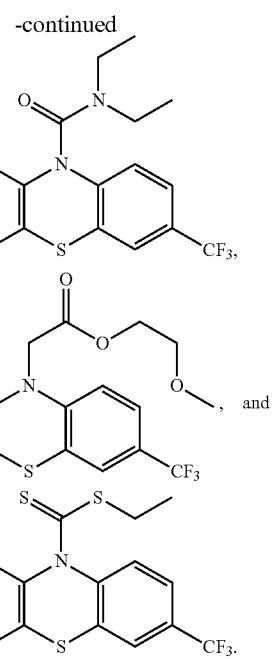

5. The battery of claim 2, wherein the compound is:

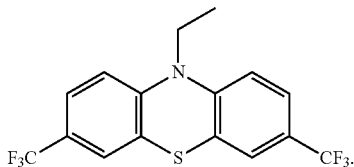

6. The battery of claim 2, wherein the first and the second non-aqueous liquid electrolyte solutions comprise a metal halide salt.

7. The battery of claim 6, wherein the metal halide salt is selected from the group consisting of: $LiBF_4$, $NaBF_4$, $LiPF_6$, $NaPF_6$, lithium bis(oxalato)borate, tetra-n-butylammonium hexafuorophosphate tetra-n-butylammonium bromide, and tetra-n-butylammonium tetrafluoroborate.

8. The battery of claim 2, wherein the first non-aqueous liquid electrolyte solution comprises a positive electrolyte.

9. The battery of claim 8, wherein cations of the positive electrolyte are selected from $Li^+$ and $Na^+$.

10. The battery of claim 8, wherein the first non-aqueous liquid electrolyte solution further comprises a solvent selected from the group consisting of: a carbonate, a nitrile, an ether, an aromatic compound, and an ester.

11. The battery of claim 2, wherein the first and the second non-aqueous liquid electrolyte solutions are the same.

12. The battery of claim 11, wherein the first and second non-aqueous liquid electrolyte solutions comprise a metal halide salt.

13. The battery of claim 12, wherein cations of the salt are selected from $Li^+$ and $Na^+$.

14. The battery of claim 12, wherein anions of the salt are selected from the group consisting of $BF_4^-$, $PF_6^-$, $ClO_4^-$, $AsF_6^-$, $CF_3SO_3^-$, $N(SO_2CF_3)^{2-}$, $N(SO_2CF_2CF_3)^{2-}$, $B(C_2O_4)^{2-}$, and $B_{12}X_6H_{(12-n)}^{2-}$, wherein X is a halogen.

15. The battery of claim 2, wherein the first non-aqueous liquid electrolyte solution comprises a positive electrolyte and the second non-aqueous liquid electrolyte solution comprises negative electrolyte.

16. The battery of claim 2, wherein the electrodes are selected from: platinum, copper, aluminum, nickel, stainless steel, acetylene black, carbon black, activated carbon, amorphous carbon, graphite, graphene, or a nanostructured carbon material, or a combination thereof.

17. The battery of claim 2 wherein the separator material is comprised of sulfonated tetrafluoroethylene-based fluoropolymer-copolymers, sulfonated poly(ether ketones), polysulfones, polyethylene, polypropylene, ethylene-propylene copolymers, polyimides, polyvinyldifluorides, porous ceramics, porous insulated metals, cation-conducting glasses, and zeolites.

18. A method of making a non-aqueous redox flow battery comprising:
   immersing a negative electrode in a first non-aqueous liquid electrolyte solution;
   immersing a positive electrode in a second non-aqueous liquid electrolyte solution;
   interposing a semi-permeable separator between the negative and positive electrodes;
wherein the second non-aqueous liquid electrolyte solution comprises a compound of the formula:

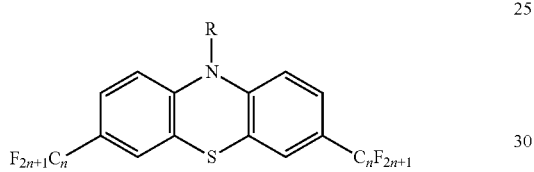

wherein R is selected from alkyl, aryl, alkylaryl, alkoxyaryl, alkylcarboxyl, aryl carbonyl, haloalkyl, perfluoroalkyl, glycols, haloaryl, a negative electrolyte, and a polymer; and
   wherein each n is independently an integer from 1 to 6.

19. The method of claim 18, wherein the compound has a solubility greater than about 0.5 M.

20. A compound selected from the group consisting of:

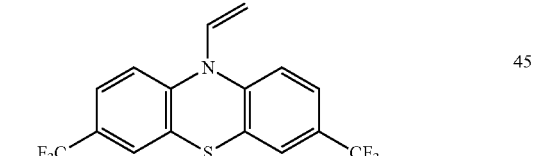

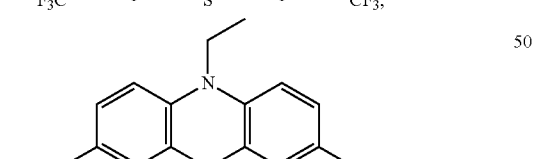

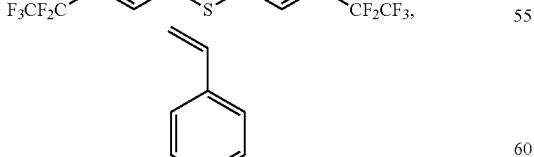

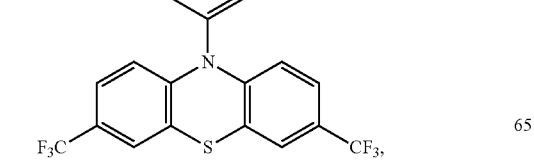

-continued

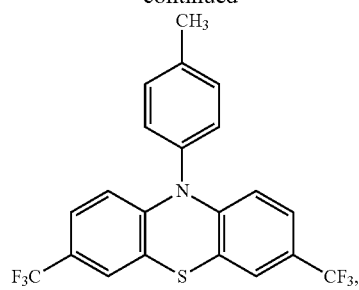

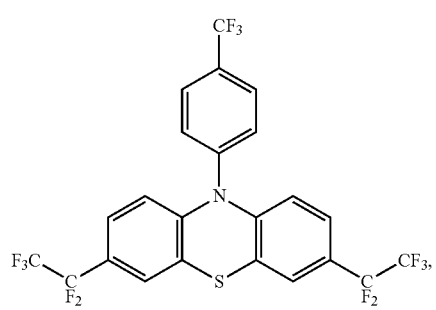

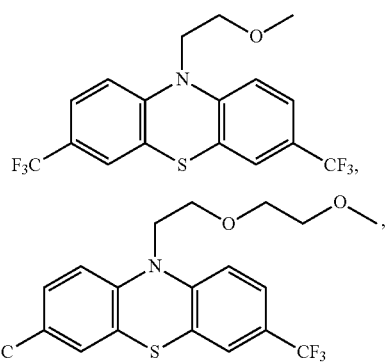

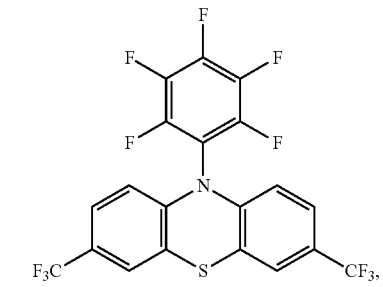

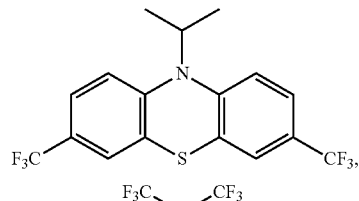

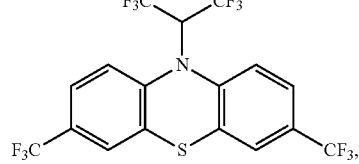

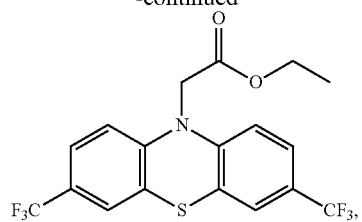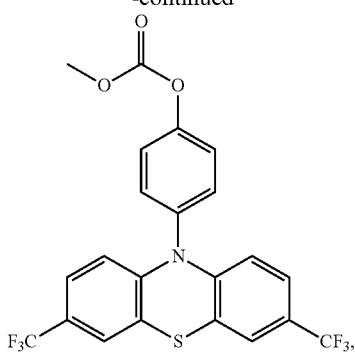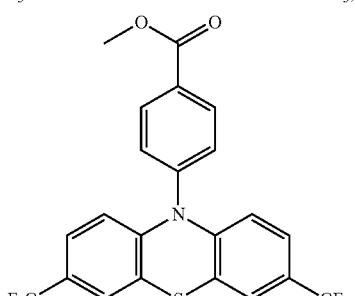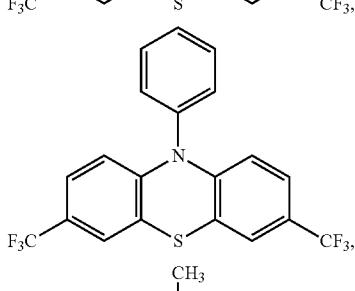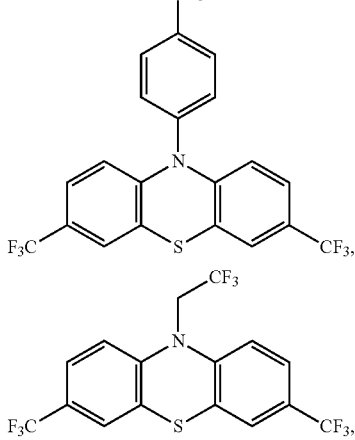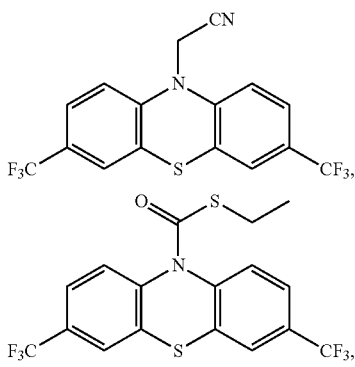

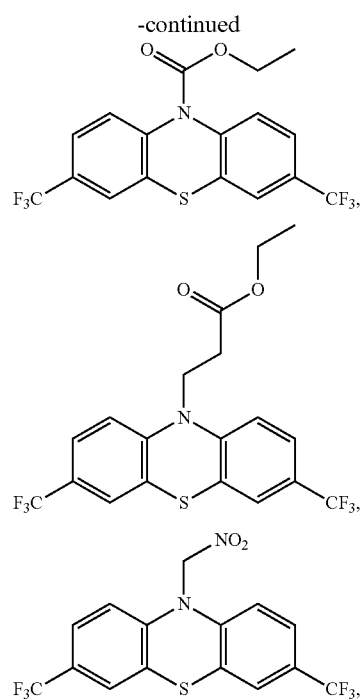
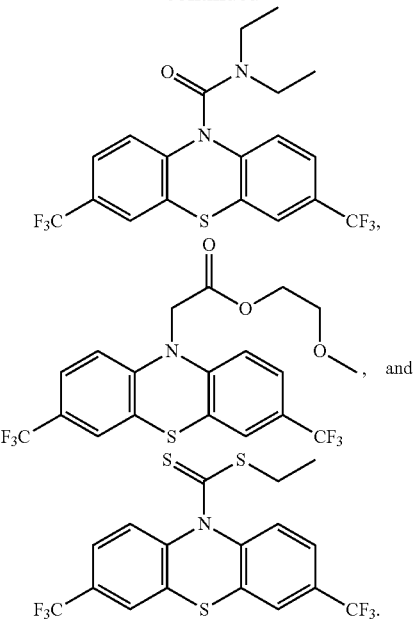
* * * * *